(12) United States Patent
Bunch et al.

(10) Patent No.: US 8,815,611 B2
(45) Date of Patent: Aug. 26, 2014

(54) SURFACE FOR LABEL INDEPENDENT DETECTION AND METHOD THEREOF

(75) Inventors: Thomas A. Bunch, Painted Post, NY (US); Sophie Deshayes, Rampillon (FR); David Henry, Morigny-Champigny (FR)

(73) Assignee: Corning Incorporated, Corning, NY (US)

( * ) Notice: Subject to any disclaimer, the term of this patent is extended or adjusted under 35 U.S.C. 154(b) by 122 days.

(21) Appl. No.: 12/417,784

(22) Filed: Apr. 3, 2009

(65) Prior Publication Data
US 2009/0258440 A1 Oct. 15, 2009

Related U.S. Application Data

(60) Provisional application No. 61/123,609, filed on Apr. 10, 2008.

(51) Int. Cl.
*G01N 33/544* (2006.01)
*C07K 1/10* (2006.01)
*G01N 33/53* (2006.01)
*G01N 33/543* (2006.01)

(52) U.S. Cl.
CPC .... *G01N 33/54353* (2013.01); *G01N 33/54393* (2013.01); *G01N 33/543* (2013.01)
USPC ............................ 436/528; 435/7.92; 530/402

(58) Field of Classification Search
None
See application file for complete search history.

(56) References Cited

U.S. PATENT DOCUMENTS

| | | | |
|---|---|---|---|
| 5,405,766 A | 4/1995 | Kallury et al. | 435/174 |
| 6,884,628 B2 | 4/2005 | Hubbell et al. | 436/518 |
| 6,905,816 B2 | 6/2005 | Jacobs et al. | 435/5 |
| 7,218,802 B1 | 5/2007 | Bellman et al. | 385/12 |
| 2002/0128234 A1 | 9/2002 | Hubbell et al. | 514/100 |
| 2004/0043508 A1 | 3/2004 | Frutos et al. | 436/518 |
| 2006/0110594 A1 | 5/2006 | Frutos et al. | 428/332 |
| 2007/0154348 A1 | 7/2007 | Frutos et al. | 422/57 |

FOREIGN PATENT DOCUMENTS

WO WO 2006/058237 6/2006
WO WO 2007/049269 5/2007

OTHER PUBLICATIONS

P. Cuatrecasas, "Protein Purification by Affinity Chromatography", *The Journal of Biological Chemistry*, 1970, vol. 245, No. 12, pp. 3059-3065.
E. Steers, Jr., et al., "The Purification of β-Galactosidase from *Escherichia coli* by Affinity Chromatography", *The Journal of Biological Chemistry*, 1971, vol. 346, No. 1, pp. 196-200.
C. Sperling, et al., "Covalently immobilized thrombomodulin inhibits coagulation and complement activation of artificial surfaces in vitro", *Biomaterials*, 2004, vol. 25, pp. 5101-5113.

*Primary Examiner* — Shafiqul Haq
(74) *Attorney, Agent, or Firm* — John L. Haack

(57) ABSTRACT

A functional group and spacer group modified polymer composition, articles incorporating the composition, and methods for label-independent-detection using the articles, as defined herein.

19 Claims, 12 Drawing Sheets

Fig. 9

| dEMA (µg/mL) | protein immo level (pm) | maximum binding | binding observed | availability % | binding Z' |
|---|---|---|---|---|---|
| 100 | 2800 | 61 | 8.15 | 13 | 0.16 |
| 75 | 2699 | 59 | 9.14 | 15 | 0.10 |
| 50 | 2547 | 56 | 9.90 | 18 | 0.51 |
| 25 | 2282 | 50 | 8.90 | 18 | 0.12 |
| 10 | 1501 | 33 | 5.66 | 17 | -0.21 |

| dEMA-PEG$_4$-sNHS (µg/mL) | protein immo level (pm) | maximum binding | binding observed | availability % | binding Z' |
|---|---|---|---|---|---|
| 100 | 3517 | 77 | 26.98 | 35 | 0.59 |
| 75 | 3358 | 73 | 25.18 | 34 | 0.61 |
| 50 | 3062 | 67 | 24.28 | 36 | 0.56 |
| 25 | 2521 | 55 | 18.86 | 34 | 0.53 |
| 10 | 1660 | 36 | 12.74 | 35 | 0.38 |

SURFACE FOR LABEL INDEPENDENT DETECTION AND METHOD THEREOF

CLAIMING BENEFIT OF PRIOR FILED U.S. APPLICATION

This application claims the benefit of U.S. Provisional Application Ser. No. 61/123,609, filed on Apr. 10, 2008. The content of this document and the entire disclosure of any publication, patent, or patent document mentioned herein is incorporated by reference.

BACKGROUND

The disclosure is related to label independent detection methods and to coated articles for label independent detection.

SUMMARY

The disclosure provides surface coat compositions, surface modified substrates for label independent detection, articles incorporating the surface modified substrates, and methods for label independent detection. The articles and methods of the disclosure can provide excellent receptivity for binding proteins and excellent sensitivity for detecting analytes.

BRIEF DESCRIPTION OF THE DRAWINGS

FIG. 9 tabulates calculated availability of protein to comparative plates and to enhanced coated plates having spacers, in embodiments of the disclosure.

DETAILED DESCRIPTION

Figure 1:
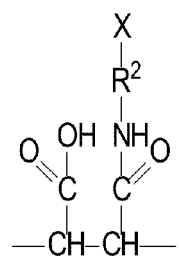
FIG. 1 is a structural segment of a polymeric coating composition, in embodiments of the disclosure.

Various embodiments of the disclosure will be described in detail with reference to drawings, if any. Reference to various embodiments does not limit the scope of the invention, which is limited only by the scope of the claims attached hereto. Additionally, examples in this specification are not limiting and merely set forth some of the many possible embodiments for the claimed invention.

Definitions

"Assay," "assaying" or like terms refers to an analysis to determine, for example, the presence, absence, quantity, extent, kinetics, dynamics, or type of a biomolecule's or a cell's optical or bioimpedance response, upon stimulation with an exogenous stimuli, such as a ligand candidate compound.

"Attached" or like term refers to any chemical interaction between two components or compounds. The type of chemical interaction that can be formed will vary depending upon the starting materials that are selected and reaction conditions. Examples of attachments described herein include, for example, covalent, electrostatic, ionic, hydrogen, or hydrophobic bonding. "Attach," "attachment," "adhere," "adhered," "adherent," "immobilized", or like terms can generally refer to immobilizing or fixing, for example, a surface modifier substance, a surface coating polymer, a compatibilizer, a cell, a ligand candidate compound, and like entities of the disclosure, to a surface, such as by physical absorption, chemical bonding, and like processes, or combinations thereof. A biosensor surface can be modified, such as having a disclosed surface coating, an anchoring or tie material, a compatibilizer (e.g., fibronectin, collagen, lamin, gelatin, polylysine, etc.), or like modifications, and combinations thereof, that can promote, for example, receptivity of the biosensor surface towards particular molecular or cellular entities, such as protein binding and ligand detection.

"Contact" or "contacting" or like terms refer to, for example, an instance of exposure by an intimate physical encounter or touching of at least one substance to another substance.

"Target" or like term refers to a cellular protein or cell-free biomolecule whose activation can mediate cell signaling or modulate cellular functions. A target can be, for example, a receptor, a phosphatase, a kinase, an enzyme, a DNA, a RNA, and like entities. A receptor can be, for example, a G protein-coupled receptor (GPCR), a receptor tyrosine kinase (RTK), a transporter, an ion channel, an integrin receptor, a sodium/proton exchanger, and like entities. A kinase can be, for example, protein kinase A, protein kinase C, mitogen-activated protein (MAP) kinases, an extracellular signal-regulated kinases, Src, Rho kinase, focal adhesion kinase, and like entities. An enzyme can be, for example, a membrane-bound adenylyl cyclase, a soluble adenylyl cyclase, a protease, and like entities.

"Screen," "screening," or like terms refers to, for example, a systematic survey of one or more compounds or drug candidates or biologicals (e.g., RNAi, antibody) to examine their pharmacological activities acting on a particular target, a cell type, or a cell system. Pharmacological or biological activity is an expression describing the beneficial or adverse effects of a drug on living matter. Aspects of the disclosure are particularly useful in biosensor-based high throughput screening (HTS) applications.

"Profile," "profiling," or like terms refers to an extrapolation of information about pharmacological activity of a drug candidate, a compound, or a biological acting on a living cell or cell system through one or more cellular targets, based on a known or predetermined signal output, such as the amplitude of an optical or bioimpedance response of cells or protein, mediated through a particular target.

"Marker" or like term refers, for example, to a molecule, a biomolecule, or a biological that is able to modulate the activities of at least one cellular target (e.g., a $G_q$-coupled receptor, a $G_s$-coupled receptor, a $G_i$-coupled receptor, a $G_{12/13}$-coupled receptor, an ion channel, a receptor tyrosine kinase, a transporter, a sodium-proton exchanger, a nuclear receptor, a cellular kinase, a cellular protein, etc.), and result in a reliably detectable biosensor output as measured by a biosensor. Depending on the class of the intended cellular target and its subsequent cellular event(s), a marker could be an activator, such as an agonist, a partial agonist, an inverse agonist, for example, for a GPCR or a receptor tyrosine kinase or an ion channel or a nuclear receptor or a cellular enzyme adenylate cyclase. The marker could also be an inhibitor for certain classes of cellular targets, for example, an inhibitor or a disrupter for actin filament, or microtubule, or an inhibitor for a kinase such as Rho kinase, or an antibody, or like entities for a cell surface molecule, such as anti-epidermal growth factor receptor antibody.

"Detect" or like term refers to an ability of the biosensor apparatus and methods of the disclosure to discover or sense, ligand-induced responses, and to distinguish the sensed responses from an absence of the ligand compound.

"Identify" or like term refers to an ability of the apparatus and methods of the disclosure to recognize a ligand compound's impact on a target and can also include an ability to classify the nature of the ligand compound's impact or interaction on the target.

"Stimulus," "therapeutic candidate compound," "therapeutic candidate," "prophylactic candidate," "prophylactic agent," "ligand candidate," "ligand compound," or like terms refer to a molecule or material, naturally occurring or synthetic, which is of interest for its potential to interact with a cellular target or isolated target immobilized or attached to the biosensor surface. A therapeutic or prophylactic candidate can include, for example, a chemical compound, a biological molecule, a peptide, a protein, a biological sample, a drug candidate small molecule, a drug candidate biologic molecule, a drug candidate small molecule-biologic conjugate, or like materials or molecular entities, and combinations thereof, which can specifically bind-to or interact-with a cellular target or isolated target such as a protein, DNA, RNA, an ion, a lipid, or like structure or component of a live-cell.

"Biosensor" or like term refers to an article, that in combination with appropriate apparatus, can detect a desired analyte. A biosensor can combine a biological component with a physicochemical detector component. A biosensor can typically consist of three parts: a biological component or element (such as tissue, microorganism, pathogen, cells, cell component, a receptor, and like entities, or combinations thereof), a detector element (operating in a physicochemical way such as optical, piezoelectric, electrochemical, thermometric, magnetic, or like manner), and a transducer associated with both components. In embodiments, the biosensor can convert a molecular recognition, molecular interaction, molecular stimulation, or like event occurring in a surface bound cell component or cell, such as a protein or receptor, into a detectable and quantifiable signal. A biosensor as used herein can include liquid handling systems which are static, dynamic, or a combination thereof. In embodiments of the disclosure, one or more biosensor can be incorporated into a micro-article. Biosensors are useful tools and some exemplary uses and configurations are disclosed, for example, in PCT Application No. PCT/US2006/013539 (Pub. No. WO 2006/108183), published Dec. 10, 2006, to Fang, Y., et al., entitled "Label-Free Biosensors and Cells," and U.S. Pat. No. 7,175,980. Biosensor-based cell assays having penetration depths, detection zones, or sensing volumes have been described, see for example, Fang, Y., et al. "Resonant waveguide grating biosensor for living cell sensing," *Biophys. J.*, 91, 1925-1940 (2006). Microfluidic articles are also useful tools and some exemplary uses, configurations, and methods of manufacture are disclosed, for example, in U.S. Pat. Nos. 6,677,131, and 7,007,709. U.S. Patent Publication 20070141231 and U.S. Pat. No. 7,175,980, disclose a microplate assembly and method.

"Hydrocarbon," "hydrocarbyl," and like terms, in the context of the tie-layer compounds, the spacer, the first monomer of the disclosure, and related descriptions, refer to any monovalent (—R) or divalent (—R—) moieties, and can include, for example, alkyl hydrocarbons, aromatic or aryl hydrocarbons, alkyl substituted aryl hydrocarbons, alkoxy substituted aryl hydrocarbons, heteroalkyl hydrocarbons, heteroaromatic or heteroaryl hydrocarbons, alkyl substituted heteroaryl hydrocarbons, alkoxy substituted heteroaryl hydrocarbons, and like hydrocarbon moieties, and as illustrated herein. In embodiments, the hydrocarbon of any of the tie-layer compounds, the spacer, or the first monomer of the disclosure, and like compounds or fragments, can be selected to be the same, similar to, or at least chemically or physically compatible with hydrocarbons, if any, contained in or on the substrate, such as a coating polymer, an inorganic polymer such as substrate material for example a glass or treated glass, or an organic-inorganic hybrid polymer such as a organo substituted polysiloxane, or combinations thereof.

"Include," "includes," or like terms means including but not limited to.

"About" modifying, for example, the quantity of an ingredient in a composition, concentrations, volumes, process temperature, process time, yields, flow rates, pressures, and like values, and ranges thereof, employed in describing embodiments of the disclosure, refers to, for example, variation in the numerical quantity that can occur, for example, through typical measuring and handling procedures used for making compounds, compositions, concentrates or use formulations; through inadvertent error in these procedures; through differences in the manufacture, source, or purity of starting materials or ingredients used to carry out the methods; and like considerations. The term "about" also encompasses amounts that differ due to aging of, for example, a composition, formulation, or cell culture with a particular initial concentration or mixture, and amounts that differ due to mixing or processing a composition or formulation with a particular initial concentration or mixture. Whether modified by the term "about" the appended claims include equivalents of these quantities.

"Consisting essentially of" in embodiments refers, for example, to a composition, a method of making or using a composition, formulation, or composition on the surface of a biosensor, and like articles, devices, or apparatus of the disclosure, and can include the components or steps listed in the claim, plus other components or steps that do not materially affect the basic and novel properties of the compositions, articles, apparatus, and methods of making and use of the disclosure, such as particular reactants, particular additives or ingredients, a particular agents, a particular cell or cell line, a particular surface modifier or condition, a particular ligand or drug candidate, or like structure, material, or process variable selected. Items that may materially affect the basic properties of the components or steps of the disclosure or that may impart undesirable characteristics to the present disclosure include, for example, decreased affinity of a biological or biomolecule for the coated biosensor surface at the outset, decreased affinity of the substrate surface for the coating, anomalous or contrary receptor binding activity in response to a ligand candidate or like stimulus, and like characteristics. In some instances, the foregoing examples of undesirable characteristics can instead be highly desirable and beneficial in biosensor applications of the present disclosure, such as discovery of conditions or coatings that decrease the affinity of a biological for a surface coating.

Thus, the claimed invention may suitably comprise, consist of, or consist essentially of: a biosensor coating composition including a polymer having surface groups that are highly reactive or receptive to biologicals or biomolecules in a first instance and having a resulting biomolecule bound polymer surface that is highly ligand sensitive in a second instance; a method of making a biosensor article having a highly receptive polymer surface; a method of immobilizing a biomolecule including contacting an article having a polymer modified surface as defined herein with a biomolecule; an article having a polymer modified surface; and an apparatus for label independent detection (LID) including an optical biosensor having a polymer modified contact surface.

"Optional" or "optionally" or like terms generally refer to, for example, that the subsequently described event or circumstance can or cannot occur, and that the description includes instances where the event or circumstance occurs and instances where it does not.

The indefinite article "a" or "an" and its corresponding definite article "the" as used herein means at least one, or one or more, unless specified otherwise.

Ranges can be expressed herein as from "about" one particular value, to "about" another particular value. When such a range is expressed, another aspect includes from the one particular value to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed, then "less than or equal to 10" as well as "greater than or equal to 10" is also disclosed. It is also understood that throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Disclosed are compounds, compositions, and components that can be used for, can be used in conjunction with, can be used in preparation for, or are products of the disclosed methods and compositions. These and other materials are disclosed herein, and it is understood that when combinations, subsets, interactions, groups, etc., of these materials are disclosed that while specific reference of each various individual and collective combinations and permutation of these compounds may not be explicitly disclosed, each is specifically contemplated and described herein. For example, if a number of different polymers and biomolecules are disclosed and discussed, each and every combination and permutation of the polymer and biomolecule are specifically contemplated unless specifically indicated to the contrary. Thus, if a class of molecules A, B, and C are disclosed as well as a class of molecules D, E, and F and an example of a combination molecule, A-D is disclosed, then even if each is not individually recited, each is individually and collectively contemplated. Thus, in this example, each of the combinations A-E, A-F, B-D, B-E, B-F, C-D, C-E, and C-F are specifically contemplated and should be considered disclosed from disclosure of A, B, and C; D, E, and F; and the example combination A-D. Likewise, any subset or combination of these is also specifically contemplated and disclosed. Thus, for example, the sub-group of A-E, B-F, and C-E are specifically contemplated and should be considered disclosed from disclosure of A, B, and C; D, E, and F; and the example combination A-D. This concept applies to all aspects of this disclosure including, but not limited to, steps in methods of making and using the disclosed compositions. Thus, if there are a variety of additional steps that can be performed it is understood that each of these additional steps can be performed with any specific embodiment or combination of embodiments of the disclosed methods, and that each such combination is specifically contemplated and should be considered disclosed.

Abbreviations, which are well known to one of ordinary skill in the art, may be used (e.g., "h" or "hr" for hour or hours, "g" or "gm" for gram(s), "mL" for milliliters, and "rt" for room temperature, "nm" for nanometers, and like abbreviations).

Specific and preferred values disclosed for radicals, substituents, components, ingredients, additives, cell types, pathogens, and like aspects, and ranges thereof, are for illustration only; they do not exclude other defined values or other values within defined ranges. The compounds, compositions, apparatus, and methods of the disclosure include those having any value or any combination of the values, specific values, more specific values, and preferred values described herein.

This disclosure relates to the field of biosensors for label independent detection (LID). The disclosure relates more particularly to LID biosensors surface chemistry and the method to prepare the same. This disclosure is more specifically concerned with methods for providing surfaces capable of immobilizing receptors (e.g., proteins) at higher density and providing better sensitivity with respect to detecting an analyte than previously reported. The LID biosensor of the disclosure can have a higher sensitivity for the detection of bio-molecular recognition events. The compositions, articles, and methods of the disclosure are particularly well suited for biosensors based on label independent detection (LID), such as for example an Epic® system or those based on surface plasmon resonance (SPR). The compositions, articles, and methods of the disclosure are also compatible with Dual Polarized Intereferometry (DPI), which is another type of LID sensor.

For LID and like detection techniques based, for example, on the local change of refractive index induced by the adsorption of the ligand onto an immobilized receptor, a biomolecule immobilization, for example, of about 2 ng mm$^2$ or greater is desirable. The binding signal, such as a change of refractive index attributable to a receptor-ligand interaction can be enhanced, for example, by increasing the number of the receptors immobilized on the surface to facilitate capture of a greater quantity of ligand(s), and additionally or alternatively, by increasing the activity or availability of the immobilized receptors.

One approach for immobilizing biomolecules is based in the use of anhydride chemistry, such as described in WO2006/058237 (ref. 1) and WO 2007/078873 (ref. 2). Receptors, such as proteins, have functional groups that can easily react with anhydride groups including, for example, the alpha-amine at the N-terminals, the Epsilon-amine of lysine side chains, cysteine sulfhydryl groups, phenolate ion of tyrosine residues, and the imidazolyl ring of histidines (ref. 1). Thus, copolymers containing anhydride moieties can be particularly well suited to immobilize such functionalized biomolecules without having to perform an activation step prior to immobilization. In addition, the high reactivity of an anhydride moiety at neutral pH allows an attachment under mild conditions of the anhydride copolymer onto chemically sensitive sensor surface such as those made of glass or silica which is not the case with harsh basic conditions required for polysaccharide (e.g., carboxymethyl dextran) attachment on gold chip.

Despite the large number of receptors (e.g., proteins) that can be immobilized with an anhydride based sensor surface of the prior art, a significant shortcoming is the considerable fraction of the immobilized proteins that exhibits low activity. Although not bound by theory, the low activity is believed to be attributable to the absence-of or distortion-from a native protein conformation. Consequently, the sensitivity with respect to detecting an analyte is lower than expected. To be useful in high throughput screening applications, such as drug discovery, sensitivity should high.

To obtain a detectable binding signal, the native properties of the immobilized receptor are preferably maintained at the surface and accessibility to the immobilized receptor by a ligand are preferably unaffected by the interfacial layer. With respect to improvement of receptor activity and preservation of the native conformation of the immobilized protein, polyethylene glycol (PEG) based coatings have been widely used. PEG substrate coatings can provide a hydrophilic environment and can protect a surface-immobilized protein from adsorption and denaturation on a hydrophobic surface. In that situation, the native conformation of the protein and its activity can be preserved. US 2002/0128234 (ref. 3) mentions multifunctional, polyionic copolymers having structures and properties optimized for specific applications, that can be synthesized-on or applied-to substrate surfaces for analytical and sensing purposes. The coating can be, for example, a polymer, having for example, grafted PEGs or like attached PEGs on the polymer backbone, and coating can be deposited onto a suitable substrate surface. However, because of the mono-functional nature of surface grafted PEG (e.g., PEG brushes), the immobilization density of receptors (e.g., proteins) cannot exceed a monolayer and can leads to a very low binding response of the analyte, which is inadequate for LID sensor applications.

Immobilization of a biologically active protein on a support with a monolayer of a spacer is known to improve the activity of the immobilized proteins. For example, U.S. Pat. No. 5,405,766 (ref. 4) describes the use of a monolayer forming spacer bound to a bifunctional phospholipid, which is in turn bound to a biologically active protein. Although this chemistry can improve the activity of the protein, immobilization density of proteins cannot exceed a monolayer and leads to a low binding response as the aforementioned PEG monolayer.

Spacers are known to be suitable for immobilizing a small ligand such as a drug molecule. The spacer consists of a low molecular weight molecule that acts as link or tether between a support and a ligand molecule. When a small ligand is directly attached to the support, it may not extend or protrude far enough from the support to reach the binding pocket of the molecule to be recognized, for example, a protein. Using a spacer, the result is an immobilized ligand protruding from the support or matrix surface by a distance equal to the length of the spacer which may provide good accessibility of the protein to the ligand. Cuatreacasas (ref. 5) and Steers (ref. 6) and more recently Salchert, et al. (ref. 7), and Sperling, et al. (ref. 8), mentioned the use of a spacer to immobilize small molecules. Salchert and Sperling relate to a spacer attached to maleimide copolymers to improve small molecule attachment and provide a more efficient recognition event by an approaching protein.

According to Hermanson (ref. 9) the role of a spacer in the immobilization of a large molecule, such as a protein, differs from that for immobilization of a small molecule. When immobilizing large molecular weight molecules such as proteins, the use of a spacer arm may not be as critical as it is with a small ligand. The three-dimensional size of the protein molecule is huge compared to even the longest of spacers. A spacer can extend the protein from a matrix surface by only a small percentage of the overall width of the protein. In such an instance, the results provide little if any advantage over direct attachment of the protein to the matrix with the spacer when non site-directed chemistry is used.

WO 2007/049269 (ref. 11) mentions a binding layer comprising a polysaccharide having carboxylic acid groups that exhibits high performance in binding ligand molecules and interactions with analyte molecules. The reference polysaccharide was modified by reaction with an alanine spacer. The reference mentions that the surface modification allows more efficient activation of carboxylic acid groups from the spacer compared to activation of the carboxylic acid group from a carboxymethylated polysaccharide. The reference also mentions that synthetic polymers, such as poly(acrylic acid) or poly(methacrylic acid) exhibited much more efficient activation and subsequent immobilization. However, the ligand molecules exhibited lower activity probably due to lower biocompatibility of these polymers.

Most natural polysaccharides have limited solubility in most organic solvents and are generally soluble only in water which makes the deposition or activation of the polymer in organic solvent difficult. In contrast, synthetic polymers are typically highly soluble in organic solvent(s) but may have the aforementioned lower activity. The aforementioned polysaccharides or synthetic polymers generally require an additional specific reaction or activation step to attach them onto a sensor surface because they are intrinsically unreactive. This additional step can time consuming, a source of variability, and can often require harsh conditions which are incompatible with chemically sensitive sensor surfaces, such those made of glass or silica. In embodiments, the disclosure provides surface chemistry based on synthetic polymers that can be easily attached to the LID sensor surface, that have very high immobilization capacity, i.e., capture exceeding one protein monolayer, provide good availability and activity of the immobilized biomolecule, and are compatible with label free detection sensors.

Assays using label independent detection (LID) platforms (e.g., surface plasmon resonance (SPR) or resonant waveguide grating (RWG) sensors) are typically performed using a two step procedure: i) immobilization of one of the binding partners (e.g., a protein) on the surface of the sensor; and ii) binding of a ligand (e.g., drug, protein, oligonucleotide, etc.) to the immobilized protein. Traditionally, the coupling of biomolecules to surfaces involves the activation of carboxylic acid groups on the surface to, for example, reactive N-hydroxysuccinimide (NHS) esters, which are then coupled to amino groups on the protein of interest. This method has been successfully used and commercialized by, for example, Biacore, Affinity Biosensors, and Artificial Sensing Instruments for their respective LID platforms. While effective, the activation step is time consuming and involves the handling and unnecessary use of chemicals.

An alternative approach involves the use of "preactivated" chemistries. For example, surfaces presenting aldehyde groups have been used to bind biomolecules. However, a reduction step is required after coupling to stabilize the resulting Schiff base. Surfaces with epoxide and isocyanate functionalities have also been used; however, the epoxide group is relatively slow to react and, therefore, requires long incubation times under very basic conditions, while the isocyanate group is extremely reactive and presents storage stability issues. Because of these issues, there are few reports of the use of preactivated chemistries for LID platforms.

Maleic anhydride reacts readily with nucleophiles such as amino groups. Although the modification of surfaces with maleic anhydride copolymer layers for the immobilization of small molecules, DNA, sugars, and peptides has been described, the hydrolytic stability of maleic anhydrides is rather poor, and for this reason they have not been widely used. The hydrolytic stability of maleic anhydride can be increased when copolymerized with hydrophobic monomers (e.g., styrene); however, this leads to problems with nonspecific binding of biomolecules to the surface. While this may be an advantage for some applications such as mass spectrometry, it is problematic for LID.

An aspect for useful LID methods is high biospecificity. The incorporation of "blocking agents" (e.g. bovine serum albumin, BSA) in the analyte solution is undesirable because both specific (due to the analyte) and non-specific (due to the blocking agent) binding would contribute to changes in interfacial refractive index and would be indistinguishable. This problem is only exacerbated when complex samples are used or when the analyte is impure. The concern with anhydrides for immobilization of biomolecules, for example proteins, is non-specific binding due to the formation of residual negative charge and the influence of other groups (e.g., styrene, ethylene, methyl vinyl ether, etc) in the polymer. For these reasons, use of anhydride polymers for LID is a potential concern.

The supports and methods of the disclosure provide numerous advantages. For example, the support does not need to be activated, which saves the user time, cost, and complexity. The disclosed supports and methods permit the loading of high amounts of biomolecules, which leads to better sensitivity with respect to detecting an analyte. Additionally, the methods for producing the supports permit high-volume manufacturing of the supports. In general, the supports are stable and can be stored for extended (e.g., about 6 months) periods with little or no loss in binding capacity. Moreover, the coated substrates are slow to hydrolyze under acidic conditions, which permit the binding of various biomolecules under conditions that have not been described using known techniques for polymers, for example, anhydride polymers. Finally, the supports and methods also increase array signal intensity, sensitivity and assay quality in a timely and economical manner and further improve the assay specificity.

I. Supports and Methods of Making

In embodiment, the disclosure provides a substrate coating composition for label independent detection supports comprising:

a polymer comprising:
one or more biomolecule immobilization group, that is having activity to immobilize a biomolecule ("reactive groups");
one or more substrate attachment group, that is having activity to attach the polymer to a substrate; and
one or more non-reactive group, that is having activity to enhance the activity of the immobilization groups.

The biomolecule immobilization group, substrate attachment group, and non-reactive group are further defined herein. The biomolecule immobilization group can further comprise a spacer situated between the polymer backbone and the biomolecule immobilization group or reactive group.

In embodiments, the disclosure provides supports useful for performing assays. In embodiments, a support for performing an assay comprises a substrate having a polymer directly or indirectly attached to the substrate, the polymer has a plurality of reactive groups that are capable of attaching-to or binding-with a biomolecule and a plurality of ionizable groups, the ratio of reactive groups to ionizable groups can be, for example, from about 0.5 to about 10, and the polymer can have a spacer unit or spacer groups situated between the polymer backbone and at least some of the reactive groups. In instances where the support is used for, for example, label independent detection methods, the polymer need not contain a photoactive group.

In embodiments, the disclosure provides an article for label-independent detection, the article comprising:

a substrate comprising a biomolecule-reactive contact surface composition; and optionally a tie layer having the abovementioned biomolecule-reactive contact surface composition deposited on the tie layer.

The substrate can further include one or more biomolecules attached to any of the biomolecule immobilization groups or reactive groups.

In embodiments the disclosure provides an article for label independent detection, the article comprising:

a substrate having a polymer coated contact surface comprising:
a tie layer; and
a polymer coat; and
a biomolecule attached to the contact surface.

In embodiments the disclosure provides an apparatus for label independent detection, the apparatus comprising: an optical biosensor having the aforementioned article having a polymer coated contact surface.

In embodiments, the disclosure provides an apparatus for label-independent detection, the apparatus comprising: an optical biosensor having a biomolecule-reactive contact surface comprising the abovementioned contact surface and optionally one or more biomolecules attached to or reacted with any of the biomolecule immobilization groups.

In embodiments, the disclosure provides methods for making a support, comprising:

attaching a polymer directly or indirectly to a substrate, the polymer having a plurality of reactive groups capable of attaching or binding to a biomolecule and a plurality of ionizable groups, the ratio of reactive groups to ionizable groups can be, for example, from about 0.5 to about 10.0, and the polymer can have, for example, a plurality of spacer groups, each spacer group being situated between the polymer backbone and at least some of the reactive groups.

In embodiments the disclosure provides methods for making a support, comprising:

attaching a polymer directly or indirectly to a substrate, the polymer having a plurality of biomolecule-reactive groups;

contacting the attached polymer with a spacer group reactant; and contacting the resulting attached polymer having a spacer group with a biomolecule-reactive group reactant. The biomolecule-reactive group reactant can react with the spacer group to add a biomolecule-reactive site. The biomolecule-reactive group reactant can also react with other available groups on the polymer to add additional biomolecule-reactive sites thereto, if desired.

In embodiments the method for making the abovementioned support, can further include:

contacting the resulting attached polymer having a spacer group and a reactive group with a biomolecule, to provide the support having an attached polymer having a spacer group and a biomolecule attached to at least one reactive group.

In embodiments, the disclosure provides a method of making an article, the method comprising:

providing a polymer receptive or functionalized substrate; and contacting the polymer receptive or functionalized substrate with substrate coating composition for label independent detection as defined herein.

The contacting deposits the polymer composition as a covalently attached or electrostatically attached coating having incipient, latent, or patent reactive groups and charged groups on the functionalized substrate. The functionalized substrate can be, for example, a silane reacted with a solid substrate. The disclosed articles and methods can have, for example, enhanced capacity and sensitivity for LID, such as for small molecule detection. In embodiments, the immobilized proteins can provide enhanced activity, for example, from about 2 to about 5 times or greater compared to other known synthetic surface chemistries for LID. As a result of the increased activity, increased sensitivity, and greater receptivity for protein, far less protein is consumed in an assay using the disclosed compositions, articles, and methods.

In embodiments the disclosure provides methods for using the abovementioned support for performing an assay, comprising:

providing the abovementioned support and an apparatus for label independent detection of an analyte; and contacting the support, having the attached polymer having a spacer group and a biomolecule attached to at least one reactive group, with a sample for assay of the analyte; and detecting the analyte.

a. Substrates

Suitable substrates can include, for example, a microplate, a slide, or any other material that is capable of attaching to the polymer. In embodiments, when the substrate is a microplate, the number of wells and well volume may vary depending upon, for example, the scale and scope of the analysis. Other examples of useful substrates can include, for example, a cell culture surface such as a 384-well microplate, a 96-well microplate, 24-well dish, 8-well dish, 10 cm dish, a T75 flask, or like articles.

For optical or electrical detection applications, the substrate can be, for example, transparent, impermeable, or reflecting, and electrically conducting, semiconducting, or insulating. For biological applications, the substrate material can be, for example, either porous or nonporous, and can be selected, for example, from organic or inorganic materials, or a combination thereof.

In embodiments, the substrate can be, for example, a plastic, a polymeric or co-polymeric substance, a ceramic, a glass, a metal, a crystalline material, a noble or semi-noble metal, a metallic or non-metallic oxide, an inorganic oxide, an inorganic nitride, a transition metal, and like materials, or any combination thereof. Additionally, the substrate can be configured so that it can be placed in any detection device. In one aspect, sensors can be integrated into, for example, the bottom or underside of the substrate and used for subsequent detection. These sensors can include, for example, optical gratings, prisms, electrodes, quartz crystal microbalances, and like articles. Detection methods can include, for example, fluorescence, phosphorescence, chemiluminescence, refractive index, mass, electrochemical, and like detection methods. In embodiments, the substrate can be a resonant waveguide grating sensor.

In embodiments, the substrate can include an inorganic material. Examples of inorganic substrate materials can include, for example, metals, semiconductor materials, glass, ceramic materials, and like materials. Examples of metals that can be used as substrate materials include, for example, gold, platinum, nickel, palladium, aluminum, chromium, steel, gallium arsenide, or combination thereof. Semiconductor materials used for the substrate material can include, for example, silicon and germanium. Glass and ceramic materials used for the substrate material can include, for example, quartz, glass, porcelain, alkaline earth aluminoborosilicate glass and other mixed oxides. Further examples of inorganic substrate materials can include, for example, graphite, zinc selenide, mica, silica, lithium niobate, and inorganic single crystal materials. In embodiments, the substrate can be gold or gold coated, for example, a gold sensor chip.

In embodiments, the substrate can be, for example, a porous, inorganic layer. Any of the porous substrates and methods of making such substrates disclosed, for example, in U.S. Pat. No. 6,750,023, can be used. In embodiments, the inorganic layer on the substrate comprises a glass or metal oxide. In embodiments, the inorganic layer can be, for example, a silicate, an aluminosilicate, a boroaluminosilicate, a borosilicate glass, or a combination thereof. In embodiments, the inorganic layer can be, for example, $TiO_2$, $SiO_2$, $Al_2O_3$, $Cr_2O_3$, CuO, ZnO, $Ta_2O_5$, $Nb_2O_5$, $ZnO_2$, or a combination thereof. In embodiments, the substrate can be, for example, $SiO_2$ with a layer comprising $Ta_2O_5$, $Nb_2O_5$, $TiO_2$, $Al_2O_3$, silicon nitride, or a mixture thereof, where the layer is adjacent to the surface of the $SiO_2$. The silicon nitride can be of the formula $SiN_x$, where the stoichiometry of silicon and nitrogen can vary.

In embodiments, the substrate can be, for example, an organic material. Useful organic materials can be, for example, made from polymeric materials due to their dimensional stability and resistance to solvents. Examples of organic substrate materials can be, for example, polyesters, such as polyethylene terephthalate and polybutylene terephthalate; polyvinylchloride; polyvinylidene fluoride; polytetrafluoroethylene; polycarbonate; polyamide; poly(meth) acrylate; polyhydrocarbyls such as polystyrene or polyethylene; ethylene/vinyl acetate copolymer; and like polymers, or combinations thereof.

In embodiments, the substrate can be, for example, a material that possesses groups capable of attaching one or more biomolecules. For example, the substrate can be, for example, one or more polymer described herein, that is coated onto the substrate or molded into any desired shape. Accordingly, the biomolecule and other components can be attached to the substrate.

b. Polymer

In embodiments, a polymer, also known as a binding polymer, having one or more reactive groups that can bind a biomolecule to the substrate, can be directly or indirectly attached to the substrate. The "reactive group" on the polymer permits the attachment of the polymer to the biomolecule. The reactive groups can also facilitate attachment of the binding polymer to the substrate. In embodiments, the polymer can be attached to the substrate covalently, electrostatically, or by a combination thereof. In embodiments, the polymer can have one type of reactive group, or two or more different types of reactive groups. In embodiments, two or more different types of binding polymers can be attached to the substrate.

In embodiments, the reactive group can form a covalent bond with a nucleophile, for example, an amine or thiol. The amine or thiol can be derived from the biomolecule or a molecule that is attached to the surface of the substrate (i.e., a tie layer) and used to indirectly attach the binding polymer to the substrate. Examples of reactive groups can be, for example, an anhydride, an epoxy, an aldehyde, an activated ester (e.g., n-hydroxysuccinimide (NHS), which is an ester with a leaving group), an isocyanate, an isothiocyanate, a sulfonyl chloride, a carbonate, an aryl or alkyl halide, an aziridine, a maleimide, a tresyl, a vinyl sulfone, a tosyl, an acyl azides, a carboxylic acid activated with carbodiimide, a phosphate activated with carbodiimide, a haloacetyl such as iodoacetyl, acryloyl, a disulfide and a pyridyl disulfide, and like groups, or a combination thereof. In embodiments, two or more different types of reactive groups can be present on the polymer.

Additionally, the polymer can also include, for example, a plurality of ionizable groups. Ionizable groups refer to groups that can be converted to a charged (i.e., ionic) group under particular reaction conditions or environmental conditions. For example, a carboxylic acid (—C(=O)—OH; an ionizable group) can be converted to the corresponding carboxylate (—C(=O)—O$^-$; a charged group) by treating the acid with a suitable base. The charged groups can be either positive or negative. An example of a positively charged group available in acidic media is an ammonium group (—NH$_3^+$). Examples of negatively charged groups include, for example, carboxylate, sulfonate, phosphonate, and like groups. In embodiments, two or more different types of ionizable groups can be present on the binding polymer.

The polymer can be water-soluble or water-insoluble depending upon the technique used to attach the polymer to the substrate. The polymer can be either linear or non-linear. When the polymer is non-linear, the polymer can be, for example, branched, hyperbranched, crosslinked, dendritic, or a combination thereof. The polymer can be a homopolymer or a copolymer.

In embodiments, the polymer can be, for example, a copolymer prepared from maleic anhydride and a first monomer. In embodiments, the amount of maleic anhydride in the binding polymer can be, for example, from 5% to 50%, 5% to 45%, 5% to 40%, 5% to 35%, 5% to 30%, 5% to 25%, 10% to 50%, 15% to 50%, 20% to 50%, 25% to 50%, or 30% to 50% by stoichiometry (i.e., mole ratio or molar amount) of the first monomer. In embodiments, the first monomer is selected to improve the stability of the maleic anhydride group in the polymer. In embodiments, the first monomer can reduce nonspecific binding of the biomolecule to the substrate. In embodiments, the amount of maleic anhydride monomer in the polymer can be, for example, about 50% (mol:mol) of the first monomer. In embodiments, the first monomer can be, for example, styrene, tetradecene, octadecene, methyl vinyl ether, triethylene glycol methyl vinyl ether, butylvinyl ether, divinylbenzene, ethylene, dimethylacrylamide, vinyl pyrrolidone, a polymerizable oligo(ethylene glycol) or oligo(ethylene oxide), propylene, isobutylene, vinyl acetate, methacrylate, acrylate, acrylamide, methacrylamide, and like monomers, or a combination thereof.

In embodiments, the polymer can be, for example, poly (vinyl acetate-maleic anhydride), poly(styrene-co-maleic anhydride), poly(isobutylene-alt-maleic anhydride), poly (maleic anhydride-alt-1-octadecene), poly(maleic anhydride-alt-1-tetradecene), poly(maleic anhydride-alt-methyl vinyl ether), poly(triethyleneglycol methyvinyl ether-co-maleic anhydride), poly(ethylene-alt-maleic anhydride), and like polymers, or a combination thereof.

In embodiments, the polymer can comprise a polymer having mers of the formula and as shown in FIG. 1 less the first monomer ($R^1$):

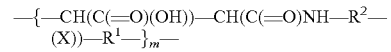

In embodiments, the polymer can comprise a copolymer having mers of the formula:

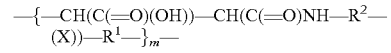

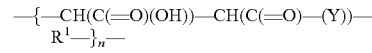

In embodiments, the polymer can comprise a copolymer having mers of the formula:

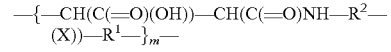

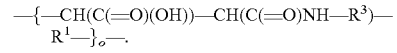

In embodiments, the polymer can comprise a copolymer having mers of the formula:

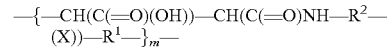

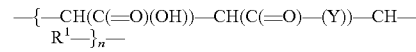

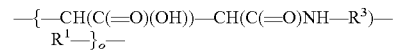

where, in the above formulas:

$R^1$ is hydrocarbyl, such as a divalent —($C_{2-6}$ alkylene)-;

$R^2$ is a divalent spacer comprising from about 6 to about 30 atoms;

$R^3$ is hydrocarbyl, such as a monovalent —($C_{1-6}$ alkyl);

X is a reactive group or a salt thereof;

Y is a surface substantive group or a salt thereof;

m is from about 10 to about 10,000;

n is from about 10 to about 10,000; and o is from about 10 to about 10,000, or a salt thereof.

In embodiments, a specific copolymer can be of the above formulas where, for example, R$^1$ is a divalent ethylene —(CH$_2$—CH$_2$)—;

R$^2$ is a divalent spacer comprising a poly alkylene glycol segment containing, for example, from about 2 to about 6 alkylene glycol units, from about 3 to about 5 alkylene glycol units, and about 4 ethylene glycol units;

R$^3$ is a monovalent propyl group;

X is a reactive group or leaving group, such as an N-hydroxysuccinimide group (NHS) or a sulfo-N-hydroxysuccinimide group (sulfo-NHS) or the salt thereof, that can be displaced or be replaced to form, for example, an amide —C(=O)—NH— linkage or like linkage with a biomolecule;

Y is a surface substantive group that is capable of forming a covalent bond or electrostatic association with the tie layer or the substrate surface, such as a carboxyl group or an amide former, —NH$_2$, —NHR, or —NR$_2$ to form an amide bond or amide linkage —C(=O)NH—, —C(=O)NHR—, or —C(=O)NR$_2$—;

m is from about 10 to about 10,000;

n is from about 10 to about 10,000; and o is from about 10 to about 10,000, or a salt thereof.

In embodiments, a specific example of the R$^2$ divalent spacer is of the formula:

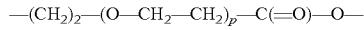

where p is from about 2 to about 6. In embodiments, the amino terminus of the spacer precursor is typically attached to the polymer backbone and the carboxy terminus is typically attached to the reactive group, although the inverse attachments are attainable.

In embodiments, another specific example of the R$^2$ divalent spacer is of the formula:

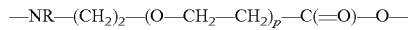

where each R is independently hydrogen or a monovalent —(C$_{1-6}$ alkyl), and p is from about 3 to about 5.

In embodiments, the polymer does not or need not contain a photoreactive or photoactive group. Photoreactive groups respond to specific applied external stimuli to undergo active species generation with resultant covalent bonding to an adjacent chemical structure, e.g., as provided by the same or a different molecule. Photoreactive groups are those groups of atoms in a molecule that retain their covalent bonds unchanged under conditions of storage; however, upon activation by an external energy source, form covalent bonds with other molecules. The photoreactive groups generate active species such as free radicals and particularly nitrenes, carbenes, and excited states of ketones upon absorption of electromagnetic energy.

c. Ratio of Reactive Groups to Ionizable Groups

In embodiments, the ratio of biomolecule reactive groups, such as NHS or sNHS, to ionizable groups, such as carboxyl —C(=O)(OH) groups, can be, for example, from about 0.01 to about 100 (0.01≤R/I≤100, where R/I represents the ratio of reactive to ionisable groups), and from about 0.1 to about 10.

When the number of reactive groups in the polymer is, for example, less than about 1% of all possible reactive and ionizable sites, the attachment of the biomolecules, while still possible will be less than highly efficient. Additionally or alternatively, if there is less than about 1% ionisable groups available of all possible reactive and ionizable sites, the attachment of the biomolecules and subsequent binding to the bound biomolecules will be less than highly efficient compared to when higher amounts of reactive and ionizable groups are present.

In embodiments, the ratio of reactive groups to ionizable groups can be, for example, from about 0.5 to about 5.0. In embodiments, the lower end of the ratio can be, for example, 0.5, 0.6, 0.7, 0.8, 0.9, 1.0, 1.5, 2.0, 2.5, 3.0, 3.5, 4.0, 4.5, or 5.0 and the upper end can be, for example, 2.0, 2.5, 3.0, 3.5, 4.0, 4.5, 5.0, 5.5, 6.0, 6.5, 7.0, 7.5, 8.0, 8.5, 9.0, 9.5, or 10.0, where any lower and upper end can form the ratio range. In embodiments, the ratio of reactive groups to ionizable groups can be, for example, from about 0.5 to 9.0, about 0.5 to 8.0, about 0.5 to 7.0, about 0.5 to 6.0, about 0.5 to 5.0, about 0.5 to 4.0, about 0.5 to 3.0, about 0.6 to 3.0, about 0.65 to 3.0, or about 0.67 to about 3.0.

One skilled in the art will recognize that a reactive group, such as an NHS, can also have an ionizable group, such as a sulfonic acid group found in for example a Sulfo-NHS. If complete activation were possible, for example with a Sulfo-NHS reagent or reactive group former, the ratio of sulfonic acid groups per NHS group would be 1, that is, 1 sulfonic acid group per NHS reactive formed. However, activation is typically not complete or is less than 100%, so that the unreacted carboxylic acid groups make the ratio of biomolecule reactive groups to ionizable groups less than 1.

The formation and number of reactive groups and ionizable groups present on the polymer can be controlled in a number of ways. In embodiments, the polymer can be synthesized from monomers possessing reactive groups and monomers with ionizable groups. In embodiments, the stoichiometry of the monomers selected can control the ratio of reactive groups to ionizable groups. In embodiments, a polymer possessing just reactive groups can be treated so that some of the reactive groups are converted to ionizable groups prior to attaching the polymer to the substrate. The starting polymer can be commercially available or synthesized using known techniques. In embodiments, a polymer can be attached to the substrate, and the attached polymer can be treated with various reagents to add either or both reactive groups and ionizable groups, or convert reactive groups to ionizable groups. In embodiments, a polymer that possesses reactive groups can be attached to the substrate, where the substrate reacts with the reactive groups and produces ionizable groups.

Figure 2:
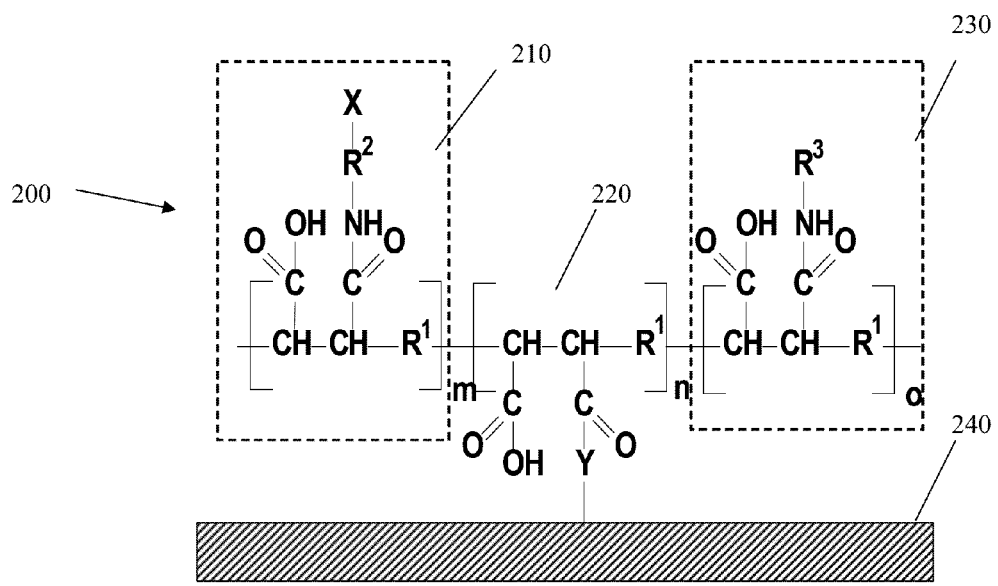
FIG. 2 shows a surface bound structural segment of a polymeric coating composition having reactive and non-reactive amic acid groups, in embodiments of the disclosure.

Referring to FIG. 2, a polymer (200) of the disclosure can have, for example, a repeat unit of {R$^1$-maleic anhydride residue}, where R$^1$ can be a residue of an unsaturated monomer that has been copolymerized with maleic anhydride, for example, ethylene, propylene, isobutylene, octadecene, tetradecene, vinyl acetate, styrene, vinyl ethers such as methyl vinyl ether, butyl vinyl ether, triethylene glycol vinylether, (meth)acrylates, (meth)acrylamide, vinyl pyrrolidinone, polymerizable oligo(ethylene glycol), oligo(ethylene oxide), and like monomers. This polymer, in solution or attached to the substrate surface, can be further reacted with a W—R$^3$ blocking agent or like agent to form, for example, a "non-reactive" group or "inactive" group or mer (230), where W is a nucleophilic group such as, for example, NH$_2$, OH, or SH, and R$^3$ can be hydrogen or a substituted or unsubstituted C$_1$-C$_6$alkyl group (linear or branched), an oligo(ethylene oxide) or oligo(ethylene glycol), or a dialkyl amine such as dimethyl amino propyl or diethyl amino propyl. As illustrated herein a "non-reactive" group or "inactive" group of mer (230) refers only to "non-reactivity" of the —NHR$^3$ substituent. The companion carboxyl group arising, for example, from anhydride opening with the W—R$^3$, like the other polymer backbone carboxyls, such as mer (210) and mer (220), is also available for reacting with a biomolecule albeit without having spacer separation from the polymer backbone. Additionally or alternatively, the carboxyl can be selectively converted to an ionic or ionizable group.

The reaction of an anhydride with a blocking agent ring-opens to produce a carboxylic acid (e.g., an ionizable group). This is referred to as pre-blocking. The pre-blocked polymer, if desired, can then be applied to the surface of the substrate (240). If the substrate possesses nucleophilic groups Y, where Y can be for example $NH_2$, OH, or SH, these groups can react with the maleic anhydride groups of surface reactive mer (220) present on the pre-blocked polymer to form a covalent bond between the pre-blocked polymer and the substrate and result in —Y—. In embodiments, the surface reactive mer (220) having reacted with the surface can have a second reactive group, such as a carboxyl group the can reacted further with, for example, a biomolecule. Thus, the unreacted carboxyl of the surface reactive mer (220) and the unreacted carboxyl of the reactive mer (210) can provide sites for reaction with a biomolecule in addition to reactive groups (X) that are attached to the polymer backbone via the spacer or tether $R^2$ of mer (210).

The ratio of reactive groups to ionizable groups can be controlled by, for example, using specific amounts of reagents. Other properties of the polymer (e.g., hydrophobicity) can be altered as needed by controlling the starting materials used to prepare the polymer (e.g., selection of hydrophobic monomers) or by appropriate choice of the derivatizing or blocking reagent. In embodiments, the ratio of reactive groups to ionizable groups can be controlled by converting one or more reactive groups (210) to inactive groups. In embodiments, from about 10% to about 50% of the reactive groups present on the polymer can be blocked or rendered inactive. The term "blocked" refers to the conversion of a reactive group present on the polymer to an inactive group, where the inactive group does not form a covalent attachment with a biomolecule. In embodiments, the amount of reactive groups that are blocked can be, for example, from about 10%, about 12%, about 14%, about 16%, about 18%, about 20%, about 22%, about 24%, about 26%, about 28%, about 30%, about 32%, about 34%, about 36%, about 38%, about 40%, about 42%, about 44%, about 46%, about 48%, or about 50%, where any value can form a lower and upper end of a range. In embodiments, the amount of reactive groups blocked can be, for example, from about 10% to about 45%, 10% to about 40%, 10% to about 35%, 15% to about 35%, 20% to about 35%, or about 25% to about 35%.

In embodiments, the blocking agent can react with the polymer prior to attaching the binding polymer to the substrate. Alternatively, the polymer can be attached to the substrate first followed by blocking with the blocking agent. In embodiments, the blocking agent can be, for example, at least one nucleophilic group, the polymer can be, for example, at least one electrophilic group, and the blocking agent can be, for example, attached to the binding polymer by a reaction between the electrophilic group and the nucleophilic group. In embodiments, the blocking agent can be, for example, covalently attached to the binding polymer. For example, when the blocking agent comprises an amine group, hydroxyl group, or thiol group, it can react with an electrophilic group present on the binding polymer (e.g., an epoxy, anhydride, activated ester group) to produce a covalent bond.

In embodiments, the blocking agent can be, for example, an alkyl amine, an alkylhydroxy amine, or an alkoxyalkyl amine. "Alkyl" can refer to a branched or unbranched saturated hydrocarbon group of 1 to about 25 carbon atoms, such as methyl, ethyl, n-propyl, isopropyl, n-butyl, isobutyl, t-butyl, pentyl, hexyl, heptyl, octyl, decyl, tetradecyl, hexadecyl, eicosyl, tetracosyl, and like groups. Examples of longer chain alkyl groups can be, for example, an oleate group or a palmitate group. A "lower alkyl" group is an alkyl group containing, for example, from one to about six carbon atoms. "Alkylhydroxy" can refer to an alkyl group as defined above where at least one of the hydrogen atoms is substituted with a hydroxyl group. "Alkylalkoxy" can refer to an alkyl group as defined above where at least one of the hydrogen atoms is substituted with an alkoxy group —OR, where R is alkyl as defined above.

In embodiments, the blocking agent can be, for example, ammonia, 2-(2-aminoethoxy)ethanol, N,N-dimethyl ethylenediamine, ethanolamine, ethylenediamine, hydroxyl amine, methoxyethyl amine, ethyl amine, isopropyl amine, butyl amine, propyl amine, hexyl amine, 2-amino-2-methyl-1-propanol, 2-(2-aminoethyl amino)ethanol, 2-(2-aminoethoxy)ethanol, dimethylethanolamine, dibutyl ethanolamine, 1-amino-2-propanol, polyethylene glycol, polypropylene glycol, 4,7,10-trioxa-1,13-tridecanediamine, polyethylene glycol, or an amine-terminated-polyethylene glycol, Trizma hydrochloride, or any combination thereof. In embodiments, the blocking agent can be, for example, water, $H_2S$, an alcohol (ROH), or alkyl thiol (RSH), where R is alkyl as defined above.

The disclosed supports having the ratio of reactive groups to ionizable groups and spacers on the polymer have advantages over prior art sensor supports. The ratio of reactive groups to ionizable groups permits increased loading or attachment (directly or indirectly with the use of a tie layer) of the polymer on the substrate. As discussed below, the attachment of the polymer to the substrate involves mild conditions and does not require preactivation with, for example, EDC/NHS. This can save time and cost in manufacturing the supports. Alternatively or additionally, one can control the ratio of reactive groups to ionizable groups with other properties of the binding polymer such as hydrophobicity or hydrophilicity, which can increase the efficiency of the support.

In embodiments, the disclosed supports can have, for example, a higher binding capacity between the support and the biomolecule. Although not desired to be limited by theory, it is believed that if more binding polymer can be loaded on the substrate then more biomolecule can be attached to the polymer. If more biomolecules can be attached to the substrate, the performance of the support can also be enhanced. In embodiments, once the biomolecule is attached to the polymer, the immobilized biomolecule is more available or accessible for binding with an analyte. In embodiments, the disclosed polymers have greater flexibility, which also permit greater binding between the polymer and the biomolecule. The disclosed polymers can provide increased binding assay sensitivity and signal-to-noise ratios.

d. Support Preparation

The amount of polymer attached to the substrate can vary depending upon, for example, the selection of the polymer, the biomolecule, and the analyte to be detected. In embodiments, the polymer can comprise at least one monolayer. In embodiments, the polymer coat on the substrate can have a thickness of, for example, from about 10 Å to about 2,000 Å. In embodiments, the thickness of the polymer can have a lower end of about 10 Å, 20 Å, 40 Å, 60 Å, 80 Å, 100 Å, 150 Å, 200 Å, 300 Å, 400 Å, or 500 Å and an upper end of about 750 Å, 1,000 Å, 1,250 Å, 1,500 Å, 1,750 Å, or 2,000 Å, where any lower end can be combined with any upper end to form the thickness range.

In embodiments, the polymer can be attached to the substrate using techniques known in the art. For example, the substrate can be dipped in a solution of the polymer. In embodiments, the polymer can be sprayed, vapor deposited, screen printed, or robotically pin printed or stamped on the substrate. This can be done either on a fully assembled substrate or on a bottom insert, e.g., prior to attachment of the bottom insert to a holey plate to form a microplate.

In embodiments, the support can be made, for example, by attaching a polymer directly or indirectly to the substrate, where the polymer has a plurality of reactive groups capable of attaching to a biomolecule. When the polymer is directly or indirectly attached to the substrate, the polymer can be attached either covalently or non-covalently (e.g., electrostatic). FIG. 2 shows one aspect of the attachment of the polymer to the substrate, where the nucleophilic group Y (e.g., an amino group, hydroxyl group, or thiol group) reacts with an anhydride group of the polymer to produce a new covalent bond.

In embodiments, when the polymer is indirectly attached to the substrate, a tie layer can be used. The tie layer can be covalently or electrostatically attached to the outer surface of the substrate. The term "outer surface" with respect to the substrate is the region of the substrate that is exposed and can be subjected to manipulation. For example, any surface on the substrate that can come into contact with a solvent or reagent upon contact is considered the outer surface of the substrate. Thus, the tie layer can be attached to the substrate and the polymer.

In embodiments, the disclosed substrates can have a tie layer covalently bonded to the substrate; however, it is also contemplated that a different tie layer can be attached to the substrate by other means in combination with a tie layer that is covalently bonded to the substrate. For example, one tie layer can be covalently bonded to the substrate and a second tie layer can be electrostatically bonded to the substrate. In embodiments, when the tie layer is electrostatically bonded to the substrate, the compound used to make the tie layer can be positively charged and the outer surface of the substrate can be treated such that a net negative charge exists so that the tie layer compound and the outer surface of the substrate form an electrostatic bond.

In embodiments, the outer surface of the substrate can be derivatized so that there are groups capable of forming a covalent bond with the tie layer. The tie layer can be directly or indirectly covalently bonded to the substrate. In instances where the tie layer is indirectly bonded to the substrate, a linker group that can covalently attach to both the substrate and the tie layer can be used. Examples of linkers include, for example, a hydrocarbyl, an alkyl, an ether, a polyether, a polyamine, a polythioether, or like groups. If a linker is not used, and the tie layer can be covalently bonded to the substrate, and is referred to as direct covalent attachment.

In embodiments, the tie layer can be derived from a compound comprising one or more reactive functional groups that can react with the binding polymer. The phrase "derived from" with respect to the tie layer refers to the resulting residue or fragment of the tie layer compound when it is attached to the substrate. The functional groups of the polymer permit the attachment of the polymer to the tie layer. In embodiments, the functional groups of the tie layer compound can be, for example, an amino, a thiol, a hydroxyl, a carboxyl, an acrylic acid, an organic and inorganic acid, an activated ester, an anhydride, an aldehyde, an epoxide, an isocyanate, an isothiocyanate, their derivatives or salts thereof, or a combination thereof.

In embodiments, the substrate can be amine-modified with, for example, a polymer comprising at least one amino group. Examples of such polymers include, for example, polylysine, polyethylenenimine, poly(allyl)amine, or silylated polyethylenenimine. In embodiments, the substrate can be modified with an aminosilane. In embodiments, the substrate can be amine modified with a mixture of silanes containing at least one amino silane or a silane bearing groups that can be, for example, converted to amine containing group, such as an epoxy silane reacted with ammonia or an isocyanato silane reacted with water. In embodiments, the tie layer can be derived from a straight or branched-chain aminosilane, aminoalkoxysilane, aminoalkylsilane, aminoarylsilane, aminoaryloxysilane, and like compounds, or salt thereof. In embodiments, the tie layer can be derived from, for example, 3-aminopropyl trimethoxysilane, N-(beta-aminoethyl)-3-aminopropyl trimethoxysilane, N-(beta-aminoethyl)-3-aminopropyl triethoxysilane, N'-(beta-aminoethyl)-3-aminopropyl methoxysilane, aminopropylsilsesquixoxane, or like compounds. Tie layer compounds or suitable alternative or equivalent compounds are commercially available or can be readily prepared, see generally for example, Pludemann, *Silane Coupling Agents*, (1982), and Gelest, Inc., (www.gelest.com).

In embodiments, when the substrate is composed of gold, the polymer can be attached to the substrate by an aminoalkylthiol, for example, 11-amino-1-undecanethiol hydrochloride.

The tie layer can be attached to any of the disclosed substrates using techniques known in the art. For example, the substrate can be dipped in a solution of the tie layer compound. In embodiments, the tie layer compound can be sprayed, vapor deposited, screen printed, or robotically pin printed or stamped on the substrate. This can be accomplished either on a fully assembled substrate or on a bottom insert, e.g., prior to attachment of the bottom insert to a holey plate to form a microplate.

In embodiments, the substrate can comprise a gold chip, the polymer can comprise a poly(ethylene-alt-maleic anhydride) indirectly attached to the substrate by an aminoalkylthiol, and the ratio of reactive groups to ionizable groups in the polymer can be, for example, from about 0.67 to about 3.0. In embodiments, the substrate can comprise a glass substrate with a layer comprising $Ta_2O_5$, $Nb_2O_5$, $TiO_2$, $Al_2O_3$, silicon nitride, $SiO_2$ or a mixture thereof the polymer can comprise a poly(ethylene-alt-maleic anhydride) indirectly attached to the substrate by a tie layer, where the tie layer can be derived from aminopropylsilane (e.g., gamma-aminopropylsilane), and the ratio of reactive groups to ionizable groups in the polymer can be from about 0.67 to about 3.0. In embodiments, the poly(ethylene-alt-maleic anhydride) can be pre-blocked with methoxyethyl amine prior to attaching the polymer to the substrate.

II. Methods of Use

In embodiments, the disclosure provides a method of immobilizing a biomolecule, the method including, for example, contacting the aforementioned polymer coated article with a biomolecule; and optionally rinsing and drying the contacted article. The biomolecule can be, for example, at least a protein or a mixture of proteins, a nucleic acid, a pathogen, a cell structural component, a cell, and like entities, or combinations thereof.

In embodiments, the disclosure provides methods for assaying an analyte with the polymer modified support. In embodiments, the method can comprise:

contacting a sample comprising the analyte with the support comprising a substrate and a polymer directly or indirectly attached to the substrate, where the polymer has a plurality of reactive groups capable of attaching to a biomolecule and a plurality of ionizable groups, the ratio of reactive groups to ionizable groups can be from about 0.5 to about 10, and at least some of the reactive groups have a spacer unit situated between the polymer backbone and the reactive groups; and detecting the bound analyte.

In embodiments, one or more different biomolecules can be attached to the substrate to produce a variety of biological sensors. In embodiments, the biomolecule can be attached covalently or electrostatically to the binding polymer. The biomolecules can exhibit specific affinity for another molecule through covalent or non-covalent bonding. Examples of useful biomolecules can include, for example, a nucleic acid molecule, an antibody, a peptide, a small molecule, a lectin, a modified polysaccharide, a synthetic composite macromolecule, a functionalized nanostructure, a synthetic polymer, a modified or blocked nucleotide or nucleoside, a modified or blocked amino acid, a fluorophore, a chromophore, a ligand, a chelate, an aptamer, a drug (e.g., a small molecule), a hapten, and like entities, or a combination thereof.

In embodiments, the biomolecule can be, for example, a protein. The protein can include peptides, fragments of proteins or peptides, membrane-bound proteins, or nuclear proteins. The protein can be of any length, and can include one or more amino acids or variants thereof. The protein(s) can be fragmented, such as by protease digestion, prior to analysis. A protein sample to be analyzed can also be subjected to fractionation or separation to reduce the complexity of the sample. Fragmentation and fractionation can also be used together in the same assay. Such fragmentation and fractionation can simplify and extend the analysis of the proteins.

In embodiments, the biomolecule can be a virus, for example, Herpes simplex virus type-1, Herpes simplex virus type-2, Cytomegalovirus, Epstein-Barr virus, Varicella-zoster virus, Human herpesvirus 6, Human herpesvirus 7, Human herpesvirus 8, Variola virus, Vesicular stomatitis virus, Hepatitis A virus, Hepatitis B virus, Hepatitis C virus, Hepatitis D virus, Hepatitis E virus, Rhinovirus, Coronavirus, Influenza virus A, Influenza virus B, Measles virus, Polyomavirus, Human Papilomavirus, Respiratory syncytial virus, Adenovirus, Coxsackie virus, Dengue virus, Mumps virus, Poliovirus, Rabies virus, Rous sarcoma virus, Yellow fever virus, Ebola virus, Marburg virus, Lassa fever virus, Eastern Equine Encephalitis virus, Japanese Encephalitis virus, St. Louis Encephalitis virus, Murray Valley fever virus, West Nile virus, Rift Valley fever virus, Rotavirus A, Rotavirus B, Rotavirus C, Sindbis virus, Simian Immunodeficiency virus, Human T-cell Leukemia virus type-1, Hantavirus, Rubella virus, Simian Immunodeficiency virus, Human Immunodeficiency virus type-1, Vaccinia virus, SARS virus, Human Immunodeficiency virus type-2, lentivirus, baculovirus, adeno-associated virus, and like virus, or any strain or variant thereof.

In embodiments, the biomolecule can be a nucleic acid. The nucleic acid can be, for example, an oligonucleotide, deoxyribonucleic acid (DNA) or a fragment thereof, ribonucleic acid (RNA) or a fragment thereof, or peptide nucleic acid (PNA) or a fragment thereof. The nucleic acid can be a nucleic acid from any source, such as a nucleic acid obtained from cells in which it occurs in nature, recombinantly produced nucleic acid, or chemically synthesized nucleic acid. For example, the nucleic acid can be cDNA or genomic DNA or DNA synthesized to have the nucleotide sequence corresponding to that of naturally-occurring DNA. The nucleic acid can be a mutated or altered form of nucleic acid (e.g., DNA that differs from a naturally occurring DNA by an alteration, deletion, substitution or addition of at least one nucleic acid residue) or a nucleic acid that does not occur in nature.

In embodiments, the nucleic acid can be present in a vector such as an expression vector (e.g., a plasmid or viral-based vector). In embodiments, the vector can be a chromosomally integrated vector. The nucleic acids can be linear or circular, and can be of any size. In embodiments, the nucleic acid can be single or double stranded DNA or RNA.

In embodiments, the nucleic acid can be a functional nucleic acid. Functional nucleic acids are, for example, nucleic acid molecules that have a specific function, such as binding a target molecule or catalyzing a specific reaction. Functional nucleic acid molecules can be divided into categories and include, for example, antisense molecules, aptamers, ribozymes, triplex forming molecules, RNAi, and external guide sequences. The functional nucleic acid molecules can act as affectors, inhibitors, modulators, and stimulators of a specific activity possessed by a target molecule, or the functional nucleic acid molecules can possess a de novo activity independent of any other molecules.

Once the disclosed polymer has been attached to the substrate, one or more biomolecules can be attached to the polymer using the techniques mentioned above. In embodiments, when the biomolecule is a nucleic acid or protein, the nucleic acid or protein can be printed on the polymer using known techniques. The amount of biomolecule that can be attached to the polymer layer can vary depending upon, for example, the biomolecule, the polymer selected, and the analyte to be detected. In embodiments, one or more different biomolecules can be placed at different locations on the support. When different biomolecules are used, the biomolecules can be printed at the same time or different time.

In embodiments, the biomolecule can be deposited on (i.e., attached to) the support by immersing the tip of a pin into the composition comprising the biomolecule; removing the tip from the composition, where the tip comprises the composition; and transferring the composition to the support. This deposition can be accomplished, for example, by using a typographic pin array. The deposition can be carried out using, for example, an automated, robotic printer. Robotic systems are commercially available from, for example, Intelligent Automation Systems (IAS), Cambridge, Mass.

The pin can be solid or hollow. The tips of solid pins can be generally flat, and the diameter of the pins determines the volume of fluid that is transferred to the substrate. Solid pins having concave bottoms can also be used. In embodiments, to permit the printing of multiple arrays with a single sample loading, hollow pins that hold larger sample volumes than solid pins and therefore allow more than one array to be printed from a single loading can be used. Hollow pins can include printing capillaries, tweezers, and split pins. An example of a split pen is a micro-spotting pin from TeleChem International (Sunnyvale, Calif.). In embodiments, pins made by Point Tech can be used. The spotting solutions can be used in a number of commercial spotters including, for example, Genetix and Biorobotics spotters.

Any of the disclosed supports with one or more biomolecules attached thereto can be used to assay an analyte upon contact of the analyte with the support. Upon contact of the analyte with the support, a chemical interaction between the biomolecule and the analyte can occur to produce a bound analyte; however, it is possible that an interaction may occur to some extent between the polymer and the analyte. The nature of the interaction between the biomolecule and the analyte will vary depending upon the biomolecule and the analyte selected. In embodiments, the interaction between the biomolecule and the analyte can result in, for example, the formation of an electrostatic bond, a hydrogen bond, a hydrophobic bond, or a covalent bond. In embodiments, an electrostatic interaction can occur between the biomolecule and the analyte.

The analyte can be any naturally-occurring or synthetic compound. Examples of analytes that can be bound to the biomolecules on the substrate can include, for example, an oligonucleotide, a nucleic acid, a protein, a peptide, an antibody, an antigen, a hapten, or a small molecule (e.g., a pharmaceutical drug). Any of the above described biomolecules can be an analyte for the disclosed methods. In embodiments, a solution of one or more analytes can be prepared and added to one or more wells that have a biomolecule attached to the outer surface of the microplate. In embodiment, different biomolecules can be attached to different wells of the microplate; thus, it is possible to detect a number of different interactions between the different biomolecules and the analyte. In embodiments, a protein can be immobilized on the microplate to investigate the interaction between the protein and a second protein or small molecule. Alternatively, a small molecule can be immobilized on the microplate using the disclosed techniques to investigate the interaction between the small molecule and a second small molecule or protein. In embodiments, the biomolecule can be an oligonucleotide that can hybridize a second oligonucleotide (i.e., analyte). In embodiments, when the substrate is a microplate, the assay can be a high-throughput assay.

In embodiments, an array can be used in any of the disclosed methods. In embodiments, the array can comprise a plurality of biomolecules on the substrate, where the biomolecules are on discrete and defined locations on the support. Arrays have been used for a wide variety of applications such as gene discovery, disease diagnosis, drug discovery (pharmacogenomics) and toxicological research (toxicogenomics). An array can be an orderly arrangement of biomolecules. One typical method involves contacting an array of biomolecules with a target of interest to identify those compounds in the array that bind to the target. Arrays are generally described as macro-arrays or micro-arrays, the difference being the size of the sample spots. In embodiments, the array can be, for example, at least 96- or 384-distinct and defined locations.

Methods for producing arrays are known in the art. For example, Fodor et al., 1991, *Science,* 251:767-773, describe an in situ method that uses photo-protected amino acids and photo lithographic masking strategies to synthesize miniaturized, spatially-addressable arrays of peptides. This in situ method has been expanded to the synthesis of miniaturized arrays of oligonucleotides (U.S. Pat. No. 5,744,305). Another in situ synthesis method for making spatially-addressable arrays of immobilized oligonucleotides is described by Southern, 1992, *Genomics,* 13:1008-1017; see also Southern & Maskos, 1993, *Nucl. Acids Res.,* 21:4663-4669; Southern & Maskos, 1992, *Nucl. Acids Res.,* 20:1679-1684; Southern & Maskos, 1992, *Nucl. Acids Res.,* 20:1675-1678. In this method, conventional oligonucleotide synthesis reagents are dispensed onto physically masked glass slides to create the array of immobilized oligonucleotides. U.S. Pat. No. 5,807,522, describes a deposition method for making micro arrays of biological samples that involves dispensing a known volume of reagent at each address of the array by tapping a capillary dispenser on the substrate under conditions effective to draw a defined volume of liquid onto the substrate.

In embodiments, an array of nucleic acid(s) or protein(s) can be printed on any of the substrates described herein. The techniques disclosed in U.S. Published Application No. 2003/0228601, to Sabatini, can be used with respect to the different arrays and nucleic acid libraries that can be used in the disclosed methods.

In embodiments, the disclosed supports can have, for example, a surface with a reference region and a sample region. Several different deposition techniques (e.g., contact pin printing, non-contact printing, micro-contact printing, screen printing, spray printing, stamping, spraying, and like techniques) can be used to create a reference region and a sample region on a single support. The sample region permits the detection of an interaction between an analyte and the immobilized biomolecule, and the reference region permits the cancellation of spurious changes that can adversely affect the detection of the interaction between the analyte and immobilized biomolecule. In embodiments, the sample and reference regions are incorporated within the same well of a microplate.

In embodiments, a predefined area of the support with the binding polymer can be specifically deactivated by depositing a blocking or deactivating agent. For example, when the binding polymer is an amine reactive coating such as poly (ethylene-maleic anhydride) (EMA), any of the blocking agents described above can be used as the deactivating agent. Alternatively, non-amine containing reagents can be used to hydrolyze the reactive group present on the binding polymer to render it inactive. Thus, the biomolecule only binds to the sensor in the area that was not treated with the deactivating agent.

In embodiments, the biomolecule can be attached to the polymer, and the support can be exposed to a deactivating agent to inactivate or block the unprinted regions of the support, which can be used as a reference region.

Once the support with the attached biomolecules(s) has been contacted with the analyte, the bound analyte can be detected. As described above, one beneficial result of the disclosed substrates is that non-specific binding of the analyte can be reduced.

In embodiments, the bound analyte can be labeled for detection purposes. Depending upon the detection technique used, in embodiments, the analyte can be labeled with a detectable tracer prior to detection. The interaction between the analyte and the detectable tracer can include any chemical or physical interaction including, for example, a covalent bond, an ionic interaction, or a Lewis acid-Lewis base interaction. A "detectable tracer" refers to any compound that 1) has at least one group that can interact with the analyte, and 2) has at least one group that is capable of detection using known techniques. In embodiments, the analyte can be labeled prior to contacting the support. In embodiments, the analyte can be labeled after it has been contacted with the support. Examples of detectable tracers include, for example, fluorescent and enzymatic tracers.

In embodiments, detection of the bound analyte can be accomplished with techniques including, for example, fluorescence, phosphorescence, chemiluminescence, bioluminescence, Raman spectroscopy, optical scatter analysis, mass spectrometry, and like methods, and other generally known techniques. In embodiments, the bound analyte can be detected by label-independent detection (LID) methods. Examples of LID include, for example, a refractive index sensor (e.g., surface plasmon resonance, a resonant waveguide grating system, ellipsometry, or like index methods), an acoustic wave sensor, or a mass sensor such as mass spectrometry or a quartz crystal microbalance.

In embodiments, the disclosed supports and methods permit the loading of significant amounts of biomolecules, which can provide better sensitivity with respect to detecting an analyte. The disclosed supports and methods are also compatible with a number of different substrates, which have a broad range of applications. The preparation of the disclosed supports use mild conditions, and the resultant supports exhibit good storage stability, and have consistent, reproducible attachment of biomolecules to the substrate. Finally, the disclosed supports and methods can also increase array signal intensity, sensitivity, and assay quality in a timely and economical manner, and further improve the assay specificity.

In embodiments, the disclosure provides surface compositions for use in, for example, label-free or label-independent-detection (LID) sensors, and more specifically for binding biomolecules. In embodiments, the compositions can comprise, for example, a synthetic polymer-coated LID substrate. The coated sensors of the disclosure can have benefits in bioassays when compared to currently available coated sensors.

The polymers of the disclosure, when attached to the sensor surface, can contain at least one reactive group, such as an amic-acid group having at least one reactive side group for binding a biomolecule. Amic acids are nitrogenized acids, i.e., compounds containing both carboxylic acid and amide group. The amic-acid groups of the disclosed polymers can have the general formula of FIG. 1 where, for example, $R^2$ is a spacer, such as a linear aliphatic chain or an oxygenated aliphatic chain, and X can be, for example, a reactive group, a non-reactive group or both. In embodiments, X can be, for example, a reactive group for binding the biomolecules. $R^2$ can be, for example, a linear chain. $R^2$ can be, for example, an alkyl chain, a low molecular weight polyether chain, such as those containing less than about 24 alkylene glycol units, or a combination thereof. Other linear chains containing, for example, amide, ester, carbonate groups, or peptidic bonds can also be selected. In embodiments, when $R_2$ is alkyl it can have, for example, from about 3 to about 8 carbon atoms, and from about 4 to about 6 carbon atoms, and when $R^2$ is a poly(alkyleneglycol) it can have, for example, from about from 2 to about 24 alkylene glycol units such as ethylene glycol or propylene glycol units, or from about 2 to about 6 glycol units, such as 4 ethylene glycol or 4 propylene glycol units, or a combination thereof.

In embodiments, X can be, for example, any reactive group capable of binding to a biomolecule. Suitable X groups can be, for example, an N-Hydroxysuccinimide (NHS) ester or s substituted N-Hydroxysuccimide, such as a Sulfo-NHS. A Sulfo-NHS can be used for carbodiimide-promoted amide bond formation between amine group of the protein and the carboxylic acid group of the surface. Sulfo-NHS is particularly well suited because it is soluble in both water and organic solvent and is long-lived and is hydrolyzed more slowly in water (ref. 12).

We have surprisingly discovered that the disclosed coating compositions, articles, and methods permit the capture of large amounts of biomolecules, such as proteins, and additionally provide a high response for the interaction with small molecules. A high response refers to a binding response that is, for example, from about 2 to about 5 times greater than previously reported on an NHS activated carboxymethyl dextran (NHS/CM5) substrate and as described further below in Example 3. For example, the binding response for a furosemide/CAII binding assay performed on a Biacore (NHS/CM5) substrate is about 50 RU, compared to about 250 RU on a spacer and sulfo-NHS modified amic acid coated substrate of the disclosure, see, for example, FIG. 13. The coating compositions and their constituent polymers of the disclosure can be readily prepared by reaction between, for example, the amino groups from an amino acid compound with a polymer bearing anhydride groups, such as copolymers of maleic anhydride. Poly(ethylene-alt-maleic anhydride) or poly(methyl vinyl ether-alt-maleic anhydride) are, for example, excellent starting coreactant polymer materials. The anhydride reactive groups of the polymer also permit convenient attachment of the polymer to the sensor surface, for example, where the sensor has been previously coated with a tie layer having, for example, primary amino groups, such as an aminoalkyl silane, more specifically, gamma aminopropyl silane. The amino acid compound that reacts with the anhydride copolymer can be at least one of, for example, gamma amino butyric acid (GABA), amino hexanoic acid, amino octanoic acid, for example, or an amino-$PEG_n$-acid, for example, amino-$PEG_4$-acid, amino-$PEG_8$ acid, amino-$PEG_{12}$-acid, amino-$PEG_{24}$-acid, from Quanta Biodesign (www.quantabiodesign.com), and like compounds. The structure of amino-dPEG™$_8$ acid is of the formula:

In embodiments, the starting base polymer can contain reactive amic acid groups and non-reactive amic acid groups. A non-reactive amic acid refers to a side group, such as $R^3$ in FIG. 2, which is linked to the amide part of the amic acid but does not react with a biomolecule. In that situation the non-reactive amic-acid can be made by reaction of a monofunctional amino compound. Such monofunctional amino compound can be, for example, at least one of ethanolamine, methyl amine, propylamine, butylamine, methoxyethylamine, and like compounds, or combinations thereof.

In embodiments, the disclosure provides coating compositions that can be used to prepare LID sensors. The coating compositions can have very high protein immobilization capacity and can have significantly improved activity of the immobilized protein. In embodiments, "high protein immobilization capacity" means, for example, at least two times and even five times greater than previously reported and as comparatively described further in Example 3. For example, this correspond to a CAII immobilization response on Biacore instrument of 33,500 RU with the article and method of the present disclosure (about 33.5 ng of proteins/mm², assuming 1,000 RU response correspond to about 1 ng/mm² protein immobilized) whereas only about 6,950 RU was obtained using a NHS/CM5 in a Biacore set up and only 6,900 RU as reported by Myszka et al., "Comparative analysis of 10 small molecules binding to carbonic anhydrase II by different investigators using Biacore technology", *Analytical Biochemistry*, 359 (2006) 94-105.

The article of the present disclosure, such as a label-free detection biosensor, that incorporates any of the disclosed coatings, can provide a high sensitivity to biomolecular recognition events between, for example, a low molecular weight analyte and a high molecular weight surface bound receptor, such as a protein. The immobilized proteins exhibit enhanced activity, for example, about 2 to about 10 times greater, and from about 2 to about 6 times greater, compared to other surface chemistries such as those made of a polymer bearing only anhydride groups, see for example, copending US patent application publication US2007/0154348, to Frutos, et al.

The enhanced sensitivity of the sensor coatings and articles prepared accordingly to the disclosure can be compatible with, for example, high throughput screening (HTS) system formats used in, for example, drug discovery or other small molecule discovery studies.

The disclosure permits the preparation of sensors for label-free detection using, for example, low protein concentrations, which can further provide label-free or label-independent assays having significantly reduced costs and time horizons compared to other less sensitive LID techniques. Low protein concentration means that an assay can be performed using, for example, about 25 µg/mL of protein solution, and even 10 µg/mL or less of protein solution. Conventional assays are typically performed using higher protein concentrations of, for example, about 250 µg/mL (see Myszka, et al., supra).

The surface chemistry of the surface coatings of the disclosure can be readily implemented and are compatible with many or all label-free detection platforms, such as based on SPR, resonant grating such as an Epic® biosensor plate (from Corning Inc.), Dual Polarization Interferometry (DPI), and optionally including a micro-fluidic handling system.

Figure 3:
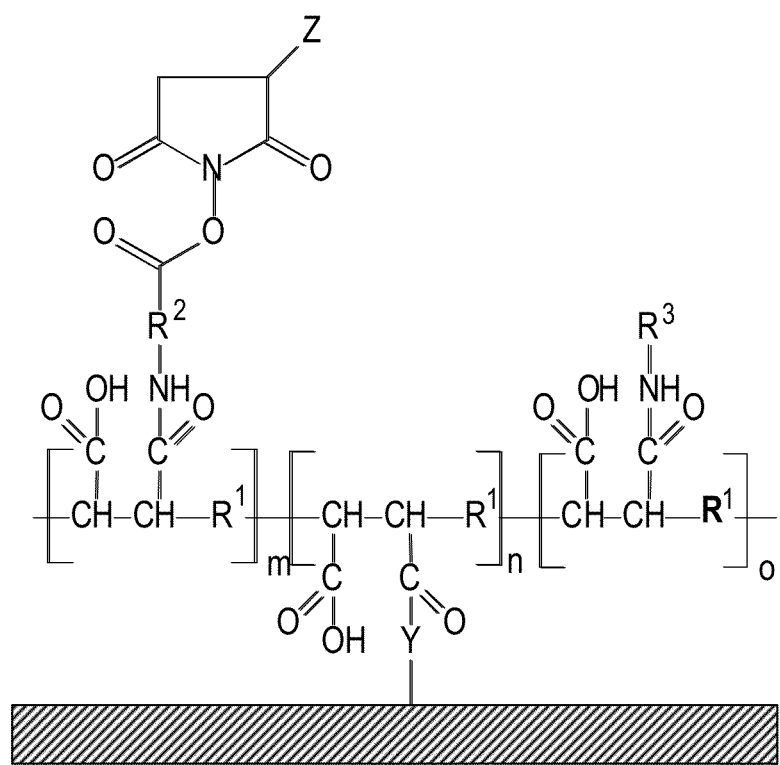
FIG. 3 shows an example of a surface bound structural segment of a polymeric coating composition having reactive and non-reactive amic acid groups, in embodiments of the disclosure.

Referring again to the Figures, FIG. 3 shows a general formula of a specific surface associated polymer of the disclosure, where, for example:

$R^1$ can be an ethylene residue —($CH_2$—$CH_2$)—;
$R^2$ can be a spacer comprising from about 6 carbon atoms, or a polyethylene glycol segment containing, for example, 4 ethylene glycol units;
$R^3$ can be a propyl group, or like alkyl groups;
Z can be, for example, a sulfonic acid group or the salt of the sulfonic acid group associated with the N-Hydroxysuccinimide reactive ester group;
Y can be an amide bond of a surface or tie layer NH;
m can be from about 10 to about 10,000;
n can be from about 10 to about 10,000; and
o can be from about 10 to about 10,000.

Figure 4:
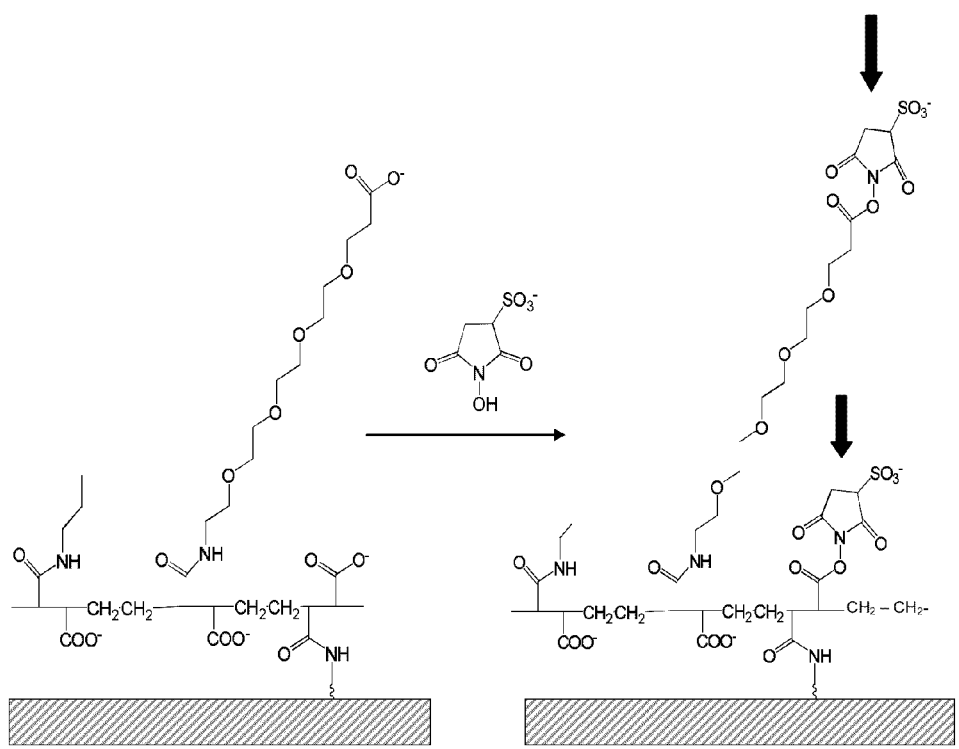
FIG. 4 shows a specific example of a surface bound structural segment of a polymeric coating composition having reactive amic acid groups and non-reactive amic acid groups, in embodiments of the disclosure.

An example of a surface modifying polymer coating of the disclosure is illustrated as a surface reaction product in FIG. 4. FIG. 4 shows the reaction of Sulfo-NHS with the surface associated polymer. The surface polymer was prepared by reaction of amino-$PEG_4$-acid with a propylamine-derivatized poly(ethylene-alt-maleic anhydride) on a commercially available Epic® plate. The resulting polymer contains reactive amic acid mers having s-NHS groups with a spacer and without a spacer (bold arrows, respectively), non-reactive amic acid mers (e.g., propyl amine), surface attached groups (e.g., —C(═O)NH—), and ionizable or ionized (shown) carboxyls.

Figure 5A:
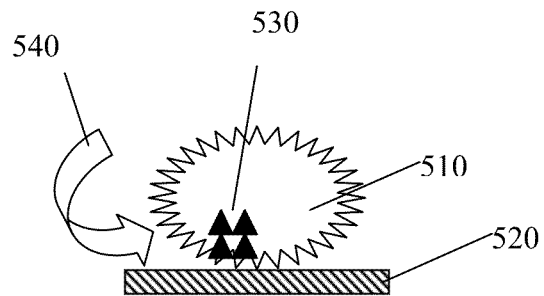
FIGS. 5A and 5B respectively illustrate ligand access restriction (5A) and ligand access enhancement (5B) to an active site of a surface bound entity, in embodiments of the disclosure.
Figure 5B:
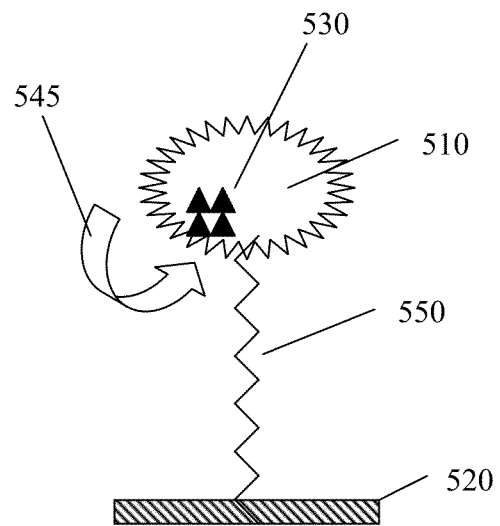

FIGS. 5A and 5B schematically illustrate examples of direct protein (e.g., Carbonic anhydrase II) immobilization on comparative derivatized surface and a derivatized surface of the disclosure, in embodiments of the disclosure. FIG. 5A shows Carbonic anhydrase II (510) immobilized on a maleic anhydride copolymer treated substrate (520)(as mentioned in WO2006/058237 and WO 2007/078873). The immobilized Carbonic anhydrase II (510) has an active site or receptor site of interest (530) and encumbered site access (540). FIG. 5B shows Carbonic anhydrase II (510) having an active site or receptor site of interest (530) immobilized on an amic-acid and spacer derivatized (550) surface (520) of the disclosure. The stylized arrows in FIGS. 5A and 5B, indicate respectively, the encumbered or limited access (540) and generous or unencumbered access (545) of a small molecule candidate to a receptor binding site or active site of the immobilized protein.

Figure 6:
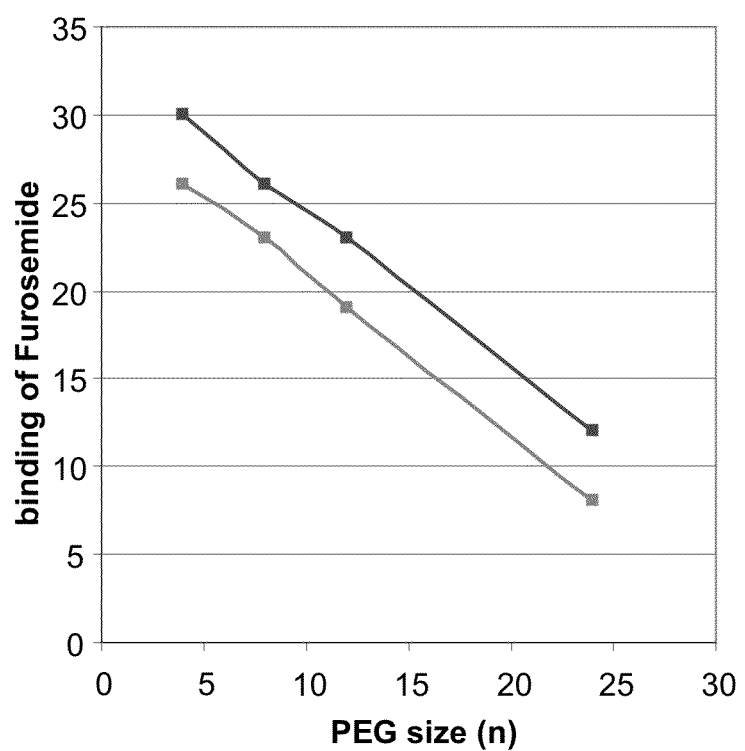
FIG. 6 shows a declining trend for activation with Sulfo-NHS for carbonic anhydrase II (CAII) immobilization in two different solvents as the spacer length increases, in embodiments of the disclosure.

FIG. 6 demonstrates the relation of the length of the spacer on the activation with Sulfo-NHS (sNHS) for carbonic anhydrase II (CAII) immobilization where line (610) represents data points for surface polymers of the disclosure having sNHS reactive groups activated in water, and line (620) represents data points for surface polymers of the disclosure having sNHS reactive groups activated in DMSO. Surprisingly, PEG spacers that were longer than about n=4 provided a consistently lower binding response. Although not limited by theory it is believed that, for example, the longer PEG modifications may be less accessible or have lower binding response because they may repel the protein due to their hydrophilic behaviour and excluded volume. This may also be why PEGs prevent non-specific protein adsorption and why PEGs prevent denaturation of the proteins. So while the PEGs may act as a spacer they may also repel the protein if spacer's molecular weight is too high. Activation of the carboxylic groups of the spacer and the carboxylic groups of the backbone was accomplished in either DMSO or water. As mentioned above, NHS activation can convert carboxylic acid groups into NHS activated ester. Carboxylic acids at the ends of the spacer are converted to NHS activated esters. Depending on the relative amounts, for example, of EDC and NHS with respect to the all carboxylic acids a portion of the carboxylic acids on the polymer backbone can also be converted to NHS activated esters, see for example, FIG. 4.

Figure 7:
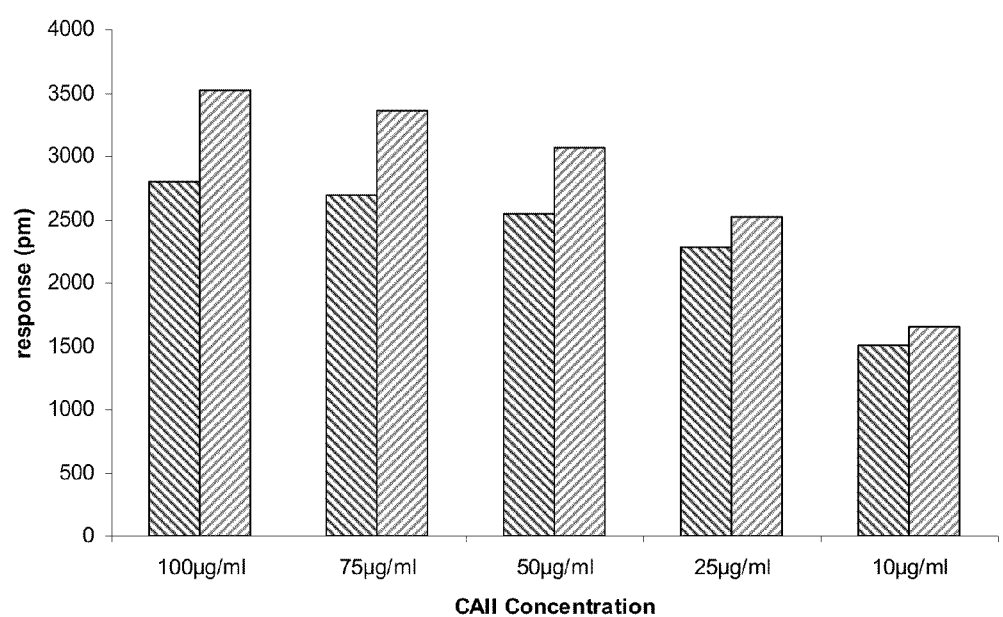
FIG. 7 shows comparative and enhanced immobilization capacity results of coated plates without and with spacers, in embodiments of the disclosure.
Figure 8:
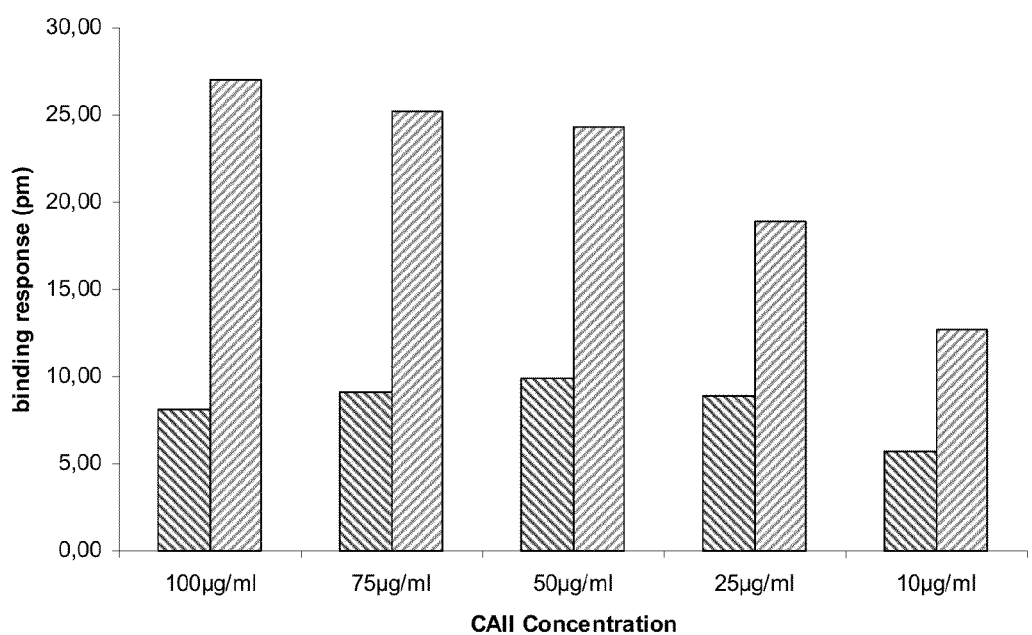
FIG. 8 shows comparative and enhanced furosemide binding capacity results of coated plates without and with spacers, in embodiments of the disclosure.

FIG. 7 shows the enhanced or superior immobilization capacity for CAII when the microplate was prepared using a reactive amic acid having spacers of the disclosure (right side bars) compared to a plate from Comparative Example 1 (left side bars). Similarly, FIG. 8 shows an exemplary vast improvement of the binding response when CAII was immobilized with the spacer based coatings of the disclosure (dEMA-$PEG_4$-sNHS; right side bars) compared with Comparative Example 1 (dEMA; left side bars)

FIG. 9 shows tabulations of calculated availability of the protein taking into account the observed binding response, the expected binding response assuming that the analyte: receptor ratio is 1:1 (stoichiometry), relative Refractive Increase Increment (RII), and molecular weight of the receptor and analyte ($M_w$). The results show that gains in availability to the receptor or access are, for example, from more than about two times to about three times using the microplate coated with the reactive amic acid of the disclosure (dEMA-$PEG_4$-sNHS) compared to the plate from Comparative Example 1. For both dEMA data (upper table) and dEMA-$PEG_4$-sNHS data (lower table) shown in FIG. 9, the $M_w$ of the drug was 331, the $M_w$ of the protein was 30,000, RII of the drug was 0.357, and the RII of the protein was 0.180.

Figure 10:
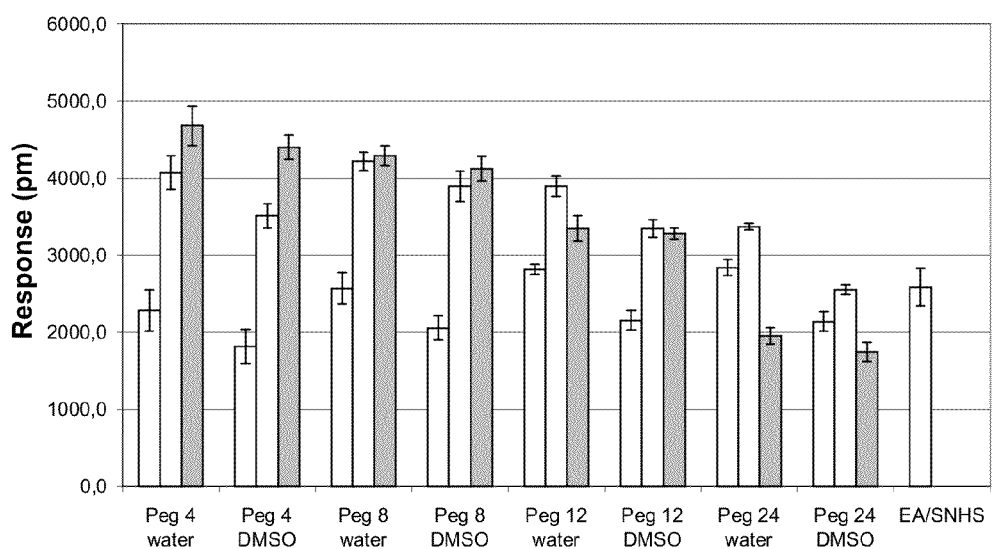
FIG. 10 charts CAII immobilization results as a function of pH and spacer length, for two different solvents, in embodiments of the disclosure.
Figure 11:
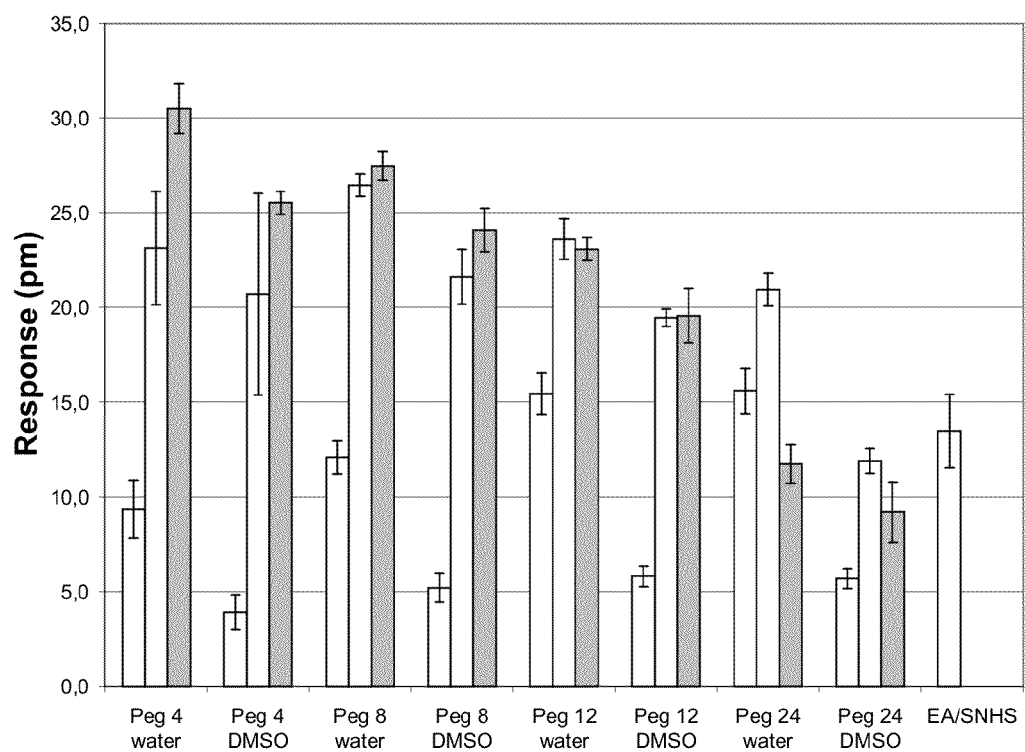
FIG. 11 charts furosemide binding results on immobilized CAII as a function of pH and spacer length, for two different solvents, in embodiments of the disclosure.

The CAII immobilization and furosemide binding responses are shown in the respective charts of FIG. 10 and FIG. 11. These CAII immobilization and furosemide binding assays were performed as described in Example 1 with the exception that the CAII was immobilized at only 100 microgram/mL in acetate buffer. Plate surfaces having various PEG mer spacer lengths (n=4, 8, 12, and 24) were evaluated in water and DMSO, at three pHs (5.8, 7.4, and 9.2, respectively), and were compared with a control (EA/sNHS at pH 5.8). The EA/NHS control refers to a polymer having all of the anhydride groups of an ethylene-maleic anhydride copolymer (dEMA) being deactivated by reaction with ethanolamine to form corresponding non-reactive amic acid residues, initially having mers of the formula:

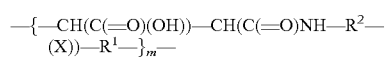

where
$R^1$ is a divalent —($CH_2$—$CH_2$)—;
$R^2$ is a divalent —($CH_2$—$CH_2$)—;
X is a —OH; and
m is from about 10 to about 10,000,
or a salt thereof,
and subsequently upon reaction with sulfo-NHS, at least mers of the formula:

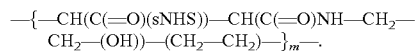

EXAMPLES

The following examples serve to more fully describe the manner of using the disclosure, and to further illustrate and demonstrate specific examples of best modes contemplated for carrying out various aspects of the disclosure. These examples do not limit the scope of the disclosure, but rather are presented for illustrative purposes.

Comparative Example 1

Direct immobilization of CAII was accomplished on a maleic anhydride copolymer which contained only non-reactive amic acid (as described in WO 2007/078873) and did not contain reactive amic acid groups. This coated product is commercially available, for example, a 384-well Corning Epic® plate available from Corning, Inc. The immobilization of the bovine carbonic anhydrase isozyme II (CAII and binding of furosemide using this comparative surface was performed as described in Example 1 below.

Comparative Example 2

Direct immobilization of CAII on maleic acid copolymer (i.e., hydrolyzed maleic anhydride copolymer) containing non-reactive amic acid and carboxylic acid activated with EDC/NHS as the comparative surface was performed as described in Example 1 below.

Example 1

Preparation of a surface having a reactive amic acid spacer A commercial Epic® Plate (Product ID 38043) having a surface coating of derivatized poly(ethylene-alt-maleic anhydride) ("dEMA"; see for example, copending US patent application publication US2007/0154348, to Frutos, et al., entitled Supports for Assaying Analytes and Methods of Making and Using Thereof, published Jul. 5, 2007) was treated as follow: 25 microliters (microL) of 400 mM aminoPEG-4 acid spacer (from QuantaBiodesign) in 50 mM borate buffer, pH 9.2, was added to each well of the plate. The solution was mixed for 5 min with a pipettor and the plate was spun down for 1 min to eliminate trapped bubbles and then incubated for about 1 hour at ambient room temperature (RT). The incubated plate was then rinsed six times with water using the pipettor. After rinsing, 25 micro liters of 200 mM EDC/50 mM Sulfo-NHS in DMSO was added to each well. The solution was mixed for 5 min. and spun down for 1 min at 800 rpm. The plate stood undisturbed for 5 min at RT. Finally, the plate was washed six times with water using the pipettor.

Protein immobilization 100, 75, 50, 25, and 10 micrograms/mL CAII in acetate buffer, pH 5.5, was added to each well of the plates prepared accordingly to Example 1 above and Comparative Example 2. Then the plates were spun down at 800 rpm for 1 min and the biomolecule immobilization was performed over about 16 hours at 4° C. The immobilization response was measured using an Epic® platform. Immobilization response is given in FIG. 7. Example 1 results are noted as dEMA-PEG$_4$-sNHS (right-side bars) and the comparative example dEMA (left-side bars).

Binding of small molecules (furosemide): A 10 microM furosemide solution was added to each well of an Epic® microplate having surface preparations as indicated above or below. An Epic® platform was used to accomplish binding assays and to record the results.

Example 2

Preparation of a surface having a reactive amic acid spacer This Example describes the results in FIGS. 10 and 11 and shows the influence of pH on the attachment of spacers having different chain lengths to the anhydride polymer. Three pHs were used to attach the spacers to the polymer: pH 9.2 (borate buffer), 7.4 (PBS) and 5.5 (acetate buffer). A commercially Epic® Plate (Product ID 38043) was treated according to the following procedure: 15 microliters of 10 mM AminoPEG-4 acid, AminoPEG-8 acid, AminoPEG-12 acid, or AminoPEG-24 acid spacer (from QuantaBiodesign) in one of the abovementioned buffers, was separately added to wells of the Epic® plate. The solution was mixed using an automated pipettor and the plate was spun down for 1 min to eliminate trapped bubbles and then incubated for about 30 min at RT. After incubation, the plate was rinsed three times with water. After rinsing, 10 microliters of 200 mM EDC/50 mM Sulfo-NHS in DMSO or water was added to each well using a 16-channel hand pipettor. The plate was spun down for 1 min at 800 rpm. The plate stood undisturbed for about 30 min at RT. Finally, the plate was washed with a plate washer. The plate was evaluated for CAII immobilization, see FIG. 10, and furosemide binding, see FIG. 11.

Example 3

SPR Biosensor Assay CAII immobilization capacity and sulfonamide (furosemide) binding evaluations were accomplished with a Biacore T100 instrument (SPR biosensor). The coating as described in Example 1 was applied on a bare gold sensor chip using an amino-siloxane-thiol tie layer consisting of a mixed polysiloxane obtained by hydrolysis and condensation of mercaptopropyl trimethoxy silane and aminopropyl triethoxysilane, and was compared to a pre-coated sensor chip ("CM5"; a carboxymethyl dextran material) of a SPR biosensor plate commercially available from Biacore. The results indicated that the SPR biosensor plate coated with the composition of Example 1 performed about five times better than the CM5 coated SPR biosensor plate.

Activation and CAII immobilization on a CM5 sensor chip: a CM5 sensor chip was used as received and without further modification. Phosphate-buffered saline (PBS), pH 7.4, was used as a running buffer. The CM5 sensor chip was activated with a 7 min injection (10 microL/min) of a 1:1 ratio of 0.4 M EDC and 0.1M NHS. CAII was coupled to the surface with a 7 min injection of 100 microg/mL CAII solution in 10 mM sodium acetate pH 5.0. Remaining groups were deactivated with a 7 min injection of 1.0 M ethanolamine pH 8.5.

Activation and CAII immobilization on the coating of Example 1: An SIA kit Au sensor chip (bare gold)(available from GE Healthcare; www.biacore.com) was first coated with a thin tie layer of the abovementioned amino-siloxane-thiol. Then a propylamine derivatized poly(ethylene-alt-maleic anhydride) coating, that is derivatized with 40 mol % propylamine, was applied on this biosensor surface as described in copending US patent application publication US2007/0154348, supra. Then the derivatized poly(ethylene-alt-maleic anhydride) coated sensor chip was treated by soaking in 5 mL of a 10 mM amino-PEG-4 acid spacer in 50 mM borate buffer, pH 9.2, for 30 min. Then the sensor chip was rinsed with water. After rinsing, the sensor surface was activated with a 12 min injection (10 microliters/min) of 1:1 ratio of 0.4 M EDC and 01M NHS. The CAII was coupled to the surface with a 7 min injection of 100 microg/mL CAII solution in 20 mM sodium acetate pH 5.0. The remaining groups were deactivated with a 7 min injection of 1.0 M ethanolamine at pH 8.

Sulfonamide (furosemide) binding: A 30 microM furosemide solution was prepared by diluting in PBS with 3% DMSO. The furosemide solution was injected with a contact time of 60 sec and a dissociation time of 900 and 300 sec, respectively, for the surface of Example 1 and the commercially available CM5 surface. To correct for the excluded volume effect, a DMSO calibration series was prepared. Sensorgrams were processed by subtracting the binding response recorded for the CM5 reference surface followed by solvent correction.

Figure 12:
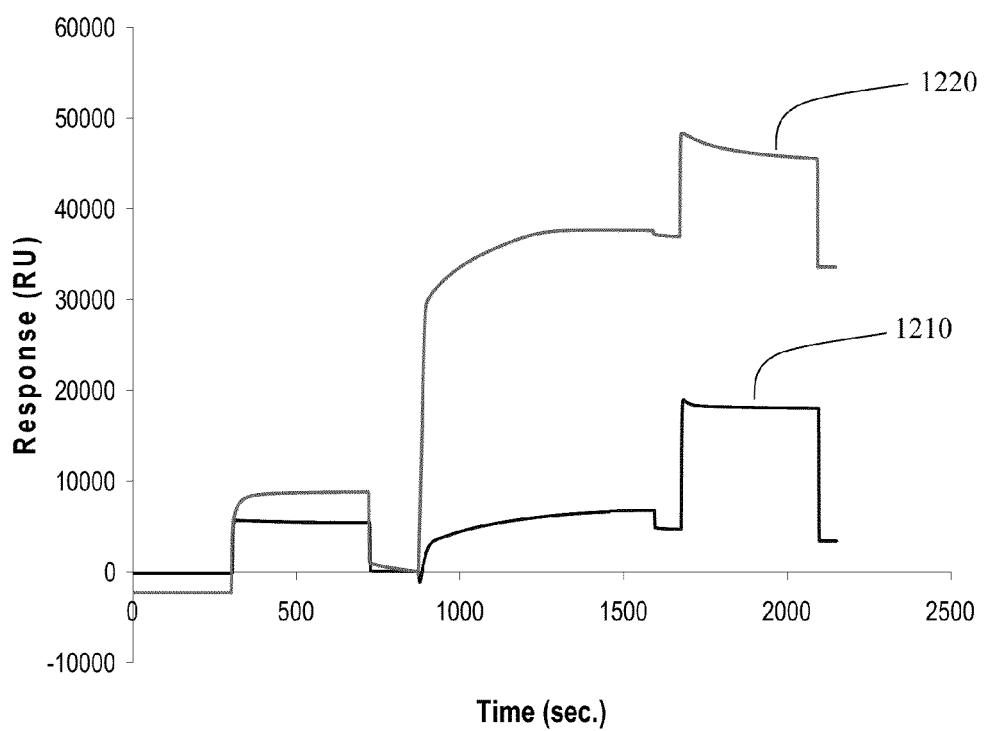
FIG. 12 shows a comparison of sensorgrams obtained for CAII immobilization with a coated product of the disclosure and a commercially coated product, in embodiment of the disclosure.

Referring to FIG. 12, FIG. 12 shows a comparison of sensorgrams obtained for the CAII immobilization with a coated plate product (1220; top trace) of the disclosure and the commercially coated CM5 plate product (1210; bottom trace). The immobilizations were about 33,520 response units for the coated plate product of the disclosure compared with about 6,950 RU for the CM5 plate. The coated plate product of the disclosure thus provides about a 5 fold (4.8) improvement compared to the commercially available CM5 coated plate product.

Figure 13:
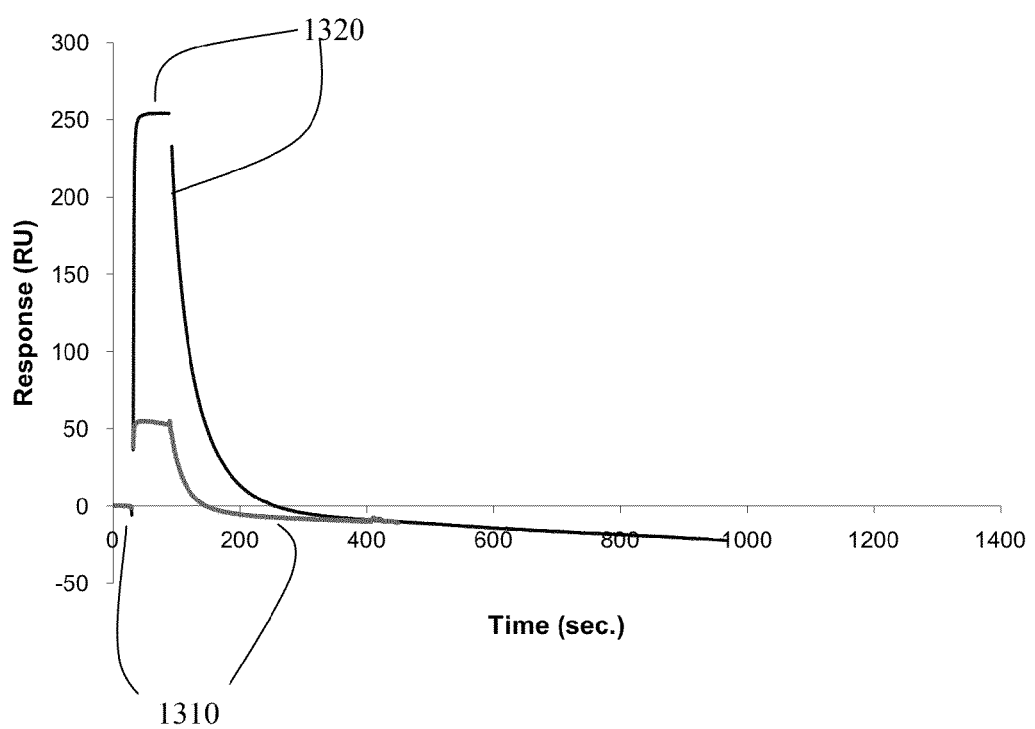
FIG. 13 shows a comparison of sensorgrams obtained for the furosemide binding with a coated product of the disclosure (top trace) and a commercially coated product (lower trace), in embodiment of the disclosure.

FIG. 13 shows a comparison of sensorgrams obtained for the furosemide binding with a coated plate of the disclosure (1320; top trace) and a commercially available coated plate (1310; bottom trace). The binding responses were 250 RU and 50 RU, respectively, for the CAII immobilized on the coated plate of Example 1 and the CM5 coated plate, for about a 5 fold relative improvement in furosemide binding.

The 6,950 response units (RU) for CAII immobilization and the 50 RU for the binding response on CM5 coated plate were in very good agreement with published data, see for example "Comparative analysis using Biacore Technology," Papalia, et al., *Anal Biochem.* 359, 94-105 (2006). These and other results demonstrate the significant gains that can be obtained with the articles and methods of the disclosure.

The disclosure has been described with reference to various specific embodiments and techniques. However, it should be understood that many variations and modifications are possible while remaining within the spirit and scope of the disclosure.

REFERENCES

1. WO2006/058237, to Frutos et al., assigned to Corning Inc., entitled "Polymer-Coated Substrates for Binding Biomolecules and Methods of Making and Using Thereof."
2. WO 2007/078873, to Frutos et al., assigned to Corning Inc., entitled "Supports for Assaying Analytes and Methods of Making and Using Thereof."
3. US 2002/0128234, to Hubbel et al., "Multifunctional polymeric surface coatings in analytic and sensor devices."
4. U.S. Pat. No. 5,405,766, to Kallury, et al., "Immobilization of biologically active protein on a support with a 7-18 carbon spacer and bifunctional phospholipids."
5. Cuatrecasas, *J. Biol. Chem.*, 245, 3059 (1970).
6. Steers, et al., *J. Biol. Chem.*, 246 196-202 (1971).
7. Salchert, et al., "Immobilization of an anticoagulant benzamidine derivative: Effect of spacer arms and carrier hydrophobicity on thrombin binding," *Acta Biomaterialia*, 1 441-449 (2005).
8. Sperling, et al., "Covalently immobilized thrombomodulin inhibits coagulation and complement activation of artificial surfaces in vitro," *Biomaterials*, 25 5101-5113 (2004).
9. Hermanson, G. T., et al., "Immobilized Affinity Ligand Techniques," Academic Press Inc., p 69 (1992)(handbook).
10. Staros, J. V., N-Hydroxysuccinimide active esters, *Biochemistry*, 21, 3950-3955(1982).
11. WO 2007/049269, to Shai, assigned to NIMRI, entitled "Binding Layer and Method for Its Preparation and Uses Thereof".
12. Greg T. Hermanson, "Bioconjugate Techniques," Academic Press Inc., p. 146, (1996) (handbook); and ref 10.

What is claimed is:

1. An assay support, comprising:
   a substrate; and
   a polymer directly or indirectly attached to the substrate, the attached polymer having a plurality of reactive groups and a plurality of inactive groups, and at least one of the reactive groups has a spacer unit ($R^2$) situated between the polymer backbone and the reactive group (X), the attached polymer comprises mers of the formula (I):

$$-\{-CH(C(=O)(OH))-CH(C(=O)NH-R^2-(X))-R^1-\}_m-$$

$$-\{-CH(C(=O)(OH))-CH(C(=O)-(Y))-CH-R^1-\}_n-$$

$$-\{-CH(C(=O)(OH))-CH(C(=O)NH-R^3)-R^1-\}_o-$$

where
   $R^1$ is a divalent hydrocarbyl residue of a first monomer;
   $R^2$ is a divalent spacer comprising from about 6 to about 30 atoms;
   $R^3$ is a monovalent hydrocarbyl;
   X is a reactive group or a salt thereof;
   Y is a surface substantive group, or a salt thereof, that directly attaches the polymer to the substrate or indirectly to a tie layer, wherein the tie layer is attached to the outer surface of the substrate;
   m is from about 10 to about 10,000,
   n is from about 10 to about 10,000; and
   o is from about 10 to about 10,000,
   or a salt thereof.

2. The support of claim 1, wherein the substrate comprises a plastic, a polymeric or co-polymeric substance, a ceramic, a glass, a metal, a crystalline material, a noble or semi-noble metal, a metallic or non-metallic oxide, an inorganic oxide, an inorganic nitride, a transition metal, or any combination thereof.

3. The support of claim 1, wherein the substrate is modified with a tie layer comprising an aminosilane, a polymer comprising at least one amino group, or a combination thereof.

4. The support of claim 1, wherein the polymer is indirectly attached to the substrate by a tie layer, and the tie layer is covalently attached, electrostatically attached, or a combination thereof, to the outer surface of the substrate.

5. The support of claim 3, wherein the tie layer is obtained from a compound comprising at least one of: a straight or branched-chain aminosilane, aminoalkoxysilane, aminoalkylsilane, aminoarylsilane, aminoaryloxysilane, aminosiloxane thiol, or a combination thereof, or a salt thereof.

6. The support of claim 3, wherein the tie layer is obtained from a compound comprising 3-aminopropyl trimethoxysilane, N-(beta-aminoethyl)-3-aminopropyl trimethoxysilane, N-(beta-aminoethyl)-3-aminopropyl triethoxysilane, N'-(beta-aminoethyl)-3-aminopropyl methoxysilane, or aminopropylsilsesquixoane.

7. The support of claim 1, wherein the reactive group comprises an anhydride, an epoxy, an aldehyde, an activated ester, a succinimide, an isocyanate, an isothiocyanate, a sulfonyl chloride, a carbonate, an aryl halide, an alkyl halide, an aziridine, a maleimide, a tresyl, a vinyl sulfone, a tosyl, an acyl azides, a carbodiimide activated carboxylic acid, a carbodiimide activated phosphate, a haloacetyl, a disulfide, a pyridyl disulfide, or a combination thereof.

8. The support of claim 1, wherein the inactive group is a positively charged group or a negatively charged group.

9. The support of claim 1, wherein the polymer, prior to attachment, comprises a copolymer of maleic anhydride and a first monomer.

10. The support of claim 9, wherein the first monomer provides the divalent hydrocarbyl (—$R^1$—) in the attached polymer and comprises styrene, tetradecene, octadecene, methyl vinyl ether, triethylene glycol methyl vinyl ether, butylvinyl ether, divinylbenzene, ethylene, acrylamide, vinyl pyrrolidone, dimethylacrylamide, a polymerizable oligo(ethylene glycol) or oligo(ethylene oxide), propylene, isobutylene, vinyl acetate, methacrylate, acrylate, methacrylamide, or a combination thereof.

11. The support of claim 1, wherein the polymer comprises at least one of poly(vinyl acetate-maleic anhydride), poly(styrene-co-maleic anhydride), poly(isobutylene-ah-maleic anhydride), poly(maleic anhydride-alt-1-octadecene), poly(maleic anhydride-alt-1-tetradecene), poly(maleic anhydride-alt-methyl vinyl ether), poly(triethyleneglycol methylvinyl ether-co-maleic anhydride), poly(ethylene-alt-maleic anhydride), or a combination thereof.

12. The support of claim 1, wherein the attached polymer comprises a poly(ethylene-alt-maleic anhydride) having reactive groups, inactive groups, and at least one spacer between the polymer backbone and one reactive group.

13. The support of claim 11, claim 1, wherein
$R^1$ is a —(—$CH_2$—$CH_2$—)—;
$R^2$ is a divalent spacer comprising a poly alkylene glycol segment containing from about 2 to about 6 alkylene glycol units;
$R^3$ is a propyl group;

X is a sulfo-N-hydroxysuccinimide group or the salt thereof;
Y is a surface substantive group;
m is from about 10 to about 10,000;
n is from about 10 to about 10,000; and
o is from about 10 to about 10,000,
and a salt thereof.

14. The support of claim 1, wherein $R^2$ comprises a divalent spacer of the formula:

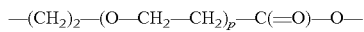

where p is from about 2 to about 6.

15. The support of claim 1, further comprising one or more biomolecules attached to the reactive group of the polymer, the biomolecule comprises a natural, synthetic or modified oligonucleotide, a natural or modified nucleotide or nucleoside, a nucleic acid (DNA or RNA) or fragment thereof, a peptide comprising natural or modified amino acid, an antibody, a hapten, a biological ligand, a chelate, an aptamer, a lipid, a saccharide, a small molecule, a lectin, a modified polysaccharide, a synthetic composite macromolecule, a functionalized nanostructure, a synthetic polymer, a fluorophore, a chromophore, or a combination thereof.

16. The support of claim 15, wherein the biomolecule is covalently attached or electrostatically attached to the polymer.

17. The support of claim 1, further comprising a plurality of biomolecules that are present on the support and wherein the biomolecules are on discrete and defined locations on the support to produce an array.

18. The support of claim 1, further comprising a biomolecule or a cell attached to the reactive group.

19. The support of claim 1, wherein the ratio of reactive groups to inactive groups is from about 0.5 to about 10.

* * * * *